(12) United States Patent
Torres

(10) Patent No.: US 10,786,192 B2
(45) Date of Patent: Sep. 29, 2020

(54) SYSTEM AND METHOD FOR DETERMINING AMOUNT OF VOLITION IN A SUBJECT

(71) Applicant: RUTGERS, THE STATE UNIVERSITY OF NEW JERSEY, New Brunswick, NJ (US)

(72) Inventor: Elizabeth B. Torres, Piscataway, NJ (US)

(73) Assignee: RUTGERS, THE STATE UNIVERSITY OF NEW JERSEY, Piscataway, NJ (US)

(*) Notice: Subject to any disclaimer, the term of this patent is extended or adjusted under 35 U.S.C. 154(b) by 0 days.

(21) Appl. No.: 16/342,858

(22) PCT Filed: Oct. 19, 2017

(86) PCT No.: PCT/US2017/057365
§ 371 (c)(1),
(2) Date: Apr. 17, 2019

(87) PCT Pub. No.: WO2018/075754
PCT Pub. Date: Apr. 26, 2018

(65) Prior Publication Data
US 2019/0261909 A1    Aug. 29, 2019

Related U.S. Application Data

(60) Provisional application No. 62/409,943, filed on Oct. 19, 2016.

(51) Int. Cl.
*A61B 5/16*     (2006.01)
*A61B 5/0402*   (2006.01)
(Continued)

(52) U.S. Cl.
CPC ............ *A61B 5/165* (2013.01); *A61B 5/0402* (2013.01); *A61B 5/0476* (2013.01);
(Continued)

(58) Field of Classification Search
CPC ...... A61B 5/165; A61B 5/0476; A61B 5/7246; A61B 5/7285
(Continued)

(56) References Cited

U.S. PATENT DOCUMENTS 6,454,729 B1    9/2002  Jacobs et al.
7,152,051 B1   12/2006  Commons et al.
(Continued)

FOREIGN PATENT DOCUMENTS

EP    1476195 B1    7/2001
EP    2801389 A1   12/2014
(Continued)

OTHER PUBLICATIONS

Herzog et al., Kinematic analysis of thalamic versus subthalamic neurostimulation in postural and intention tremor, Brain, 2007, pp. 1608-1625, vol. 130.
(Continued)

*Primary Examiner* — Amanda K Hulbert
*Assistant Examiner* — Philip C Edwards
(74) *Attorney, Agent, or Firm* — Wolter Van Dyke Davis, PLLC; Eugene J. Molinelli

(57) ABSTRACT

Provided are systems and methods for medical diagnosis. The systems and methods may identify a coherence between paired sensor data respectively measured from a first sensor attached to a head of a subject and a second sensor attached to a body part of the subject. The systems and methods may determine an amount of volition in the subject's body based on the coherence. The systems and methods may determine a diagnosis or a treatment plan for a subject based on the amount of volition. The system and methods may be used to track interaction between individuals in a clinical setting or in a social group.

20 Claims, 15 Drawing Sheets

(51) Int. Cl.

| | | |
|---|---|---|
| *A61B 5/0478* | (2006.01) | |
| *A61B 5/0488* | (2006.01) | |
| *A61B 5/055* | (2006.01) | |
| *A61B 5/08* | (2006.01) | |
| *A61B 5/11* | (2006.01) | |
| *A61B 5/00* | (2006.01) | |
| *G16H 40/63* | (2018.01) | |
| *A61B 5/0476* | (2006.01) | |
| *G16H 20/00* | (2018.01) | |
| *G16H 50/30* | (2018.01) | |

(52) U.S. Cl.
CPC .......... *A61B 5/0478* (2013.01); *A61B 5/0488* (2013.01); *A61B 5/055* (2013.01); *A61B 5/0809* (2013.01); *A61B 5/1118* (2013.01); *A61B 5/1122* (2013.01); *A61B 5/4082* (2013.01); *A61B 5/4088* (2013.01); *A61B 5/6814* (2013.01); *A61B 5/6823* (2013.01); *A61B 5/6824* (2013.01); *A61B 5/6825* (2013.01); *A61B 5/6828* (2013.01); *A61B 5/6829* (2013.01); *A61B 5/7246* (2013.01); *A61B 5/7285* (2013.01); *A61B 5/743* (2013.01); *G16H 20/00* (2018.01); *G16H 40/63* (2018.01); *G16H 50/30* (2018.01); *A61B 5/16* (2013.01); *A61B 2503/12* (2013.01); *A61B 2562/0219* (2013.01)

(58) Field of Classification Search
USPC ........................................................ 600/301
See application file for complete search history.

(56) References Cited

U.S. PATENT DOCUMENTS

| | | |
|---|---|---|
| 7,826,894 B2 | 11/2010 | Musallam et al. |
| 8,157,609 B2 | 4/2012 | Hallaian et al. |
| 8,190,251 B2 | 5/2012 | Molnar et al. |
| 2004/0030258 A1 | 2/2004 | Williams et al. |
| 2004/0096089 A1 | 5/2004 | Borsook et al. |
| 2007/0066915 A1 | 3/2007 | Frei et al. |
| 2011/0087125 A1* | 4/2011 | Causevic .................. A61B 5/04 600/544 |
| 2012/0108998 A1* | 5/2012 | Molnar .............. A61B 5/04014 600/545 |
| 2013/0178731 A1 | 7/2013 | Bosl et al. |
| 2014/0336539 A1 | 11/2014 | Torres et al. |

FOREIGN PATENT DOCUMENTS

| | | |
|---|---|---|
| WO | 2002005851 A2 | 1/2002 |
| WO | 2013052770 A1 | 4/2013 |
| WO | 2014150199 A2 | 9/2014 |

OTHER PUBLICATIONS

International Search Report in corresponding International Application No. PCT/US17/57365, dated Jan. 4, 2018.

Wang et al., "Power spectral density and coherence analysis of Alzheimer's EEG," Cognitive Neurodynamics, Dec. 16, 2014, vol. 9, p. 293, cols. 1-2, p. 294, col. 2, p. 296, col. 301, col. 1, p. 302, col. 2.

Sturman et al., "Deep brain stimulation and medication for Parkinsonian tremor during secondary tasks," Movement Disorders, vol. 8, pp. 1157-1163.

Torres et al., Characterization of the Statistical Signatures of Micro-Movements Underlying Natural Gait Patterns in Children with Phelan McDermid Syndrome: Towards Precision-Phenotyping of Behavior in ASD, Frontiers in Integrative Neuroscience, 2016, pp. 1-22, vol. 10.

Aydore et al., A Note on the Phase Locking Value and its Properties, Neuroimage, 2013, pp. 231-244, vol. 74.

Grimaldi et al., Quality parameters for a multimodal EEG/EMG/kinematic brain-computer interface (BCI) aiming to suppress neurological tremor in upper limbs, F1000Research, 2014, p. 282 vol. 2.

EP Supplemental Search Report, in application No. 17862324.5, dated Apr. 21, 2020.

* cited by examiner

SYSTEM AND METHOD FOR DETERMINING AMOUNT OF VOLITION IN A SUBJECT

CROSS-REFERENCE TO RELATED APPLICATIONS

This patent document claims priority to PCT Application No. PCT/US17/057365, filed Oct. 19, 2017, which claims priority to United States Provisional Patent Application No. 62/409,943, filed Oct. 19, 2016 under 35 U.S.C. § 119. This Provisional U.S. Application is incorporated herein by reference in its entirety.

FIELD

This document relates generally to methods and systems for determining amount of volition in a subject, and in particular to using wearable sensors to determine patient brain-body activity relationships.

BACKGROUND

The study of multiple biophysical signals has faced a challenge due to their inherent complexity, such as the different frequency ranges and spatiotemporal scales. Previous work on examining the dynamically coupled brain-body activities involves smoothing out the waveforms of interest through averaging under Gaussian, linearity, and static (stationary) assumptions. As such, there is gross data loss that hinders better understanding the interactions between the peripheral nervous system (PNS) and the central nervous systems (CNS).

In this sense, most science is either about a "disembodied brain" or a "brainless body." which is often studied by observation using descriptions of unambiguous and overt bodily motions. Such an approach tends to constrain the focus on aspects of goal-directed behavior and leave out the spontaneous/inevitable aspects of the performance, which often occurs largely beneath our conscious awareness. Further, it is unknown that how such spontaneous activity-smoothed out as "noise" or nuisance-emerges and contributes to the autonomy of the brain exerting over the body in motion. Other challenges may include misalignment of temporal landmarks from different acquisition systems and motor artifacts corrupting cortically-related signals when recording brain-body activity.

There remains a need to introduce a new platform for the personalized study of dynamically coupled brain-body activities during natural movements.

DESCRIPTION OF THE DRAWINGS

Embodiments will be described with reference to the following drawing figures, in which like numerals represent like items throughout the figures.

SUMMARY

Figure 1:
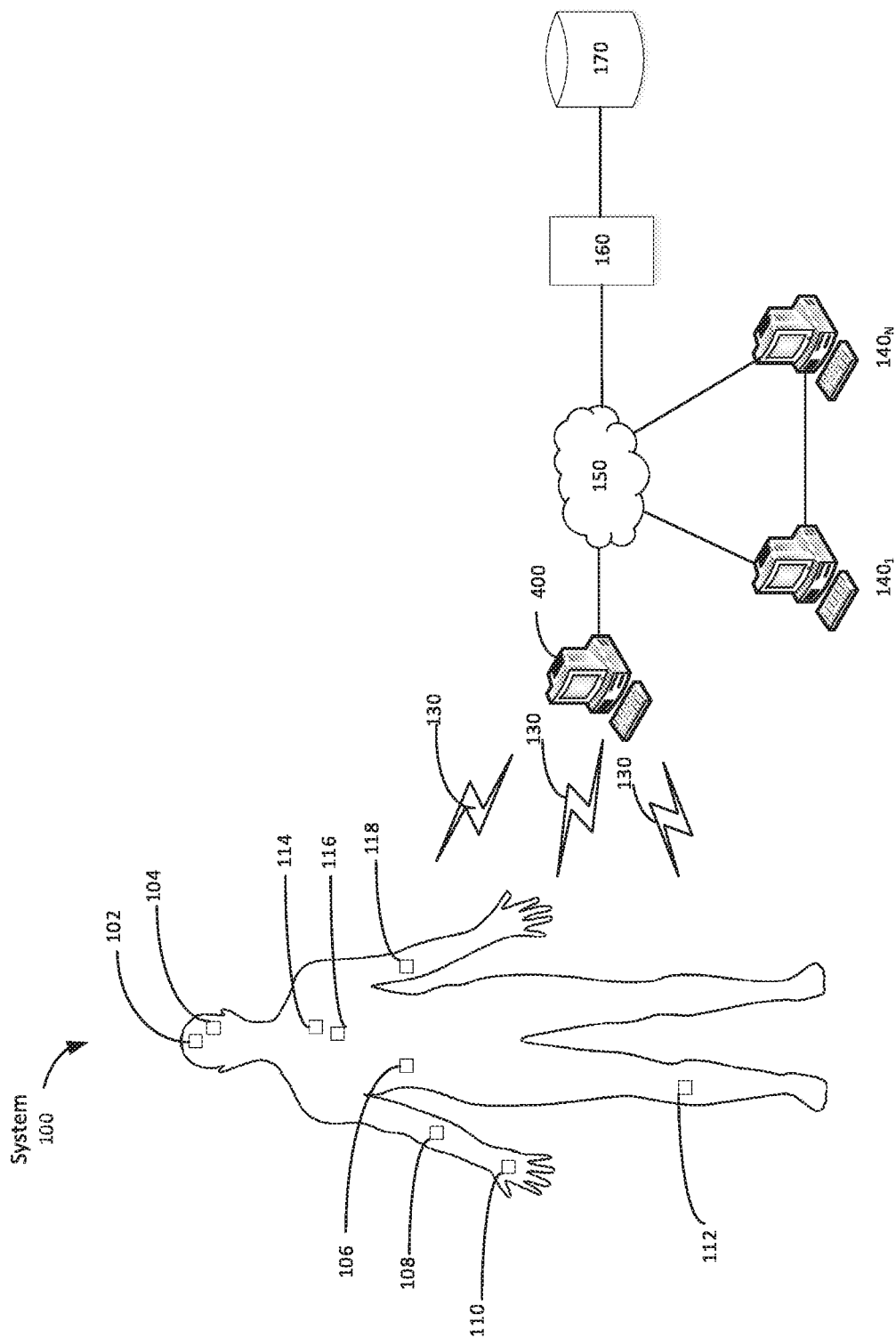
FIG. 1 illustrates an example of a system, in which sensors are attached to various locations on a human subject's body.

Systems and methods are directed to provide a medical diagnosis. A system may include a first sensor attachable to a head of a subject and configured to measure a rhythm of the subject over a recording time and generate a first series of sensor data of the subject including one or more micro-rhythm waveforms. The system may also include a second sensor attachable to a body part of the subject and configured to measure a rhythm of the subject over a recording time and generate a second series of sensor data of the subject including one or more micro-rhythm waveforms. The system may perform a power spectral analysis of a first micro-rhythm waveform in the first series of sensor data and a second micro-rhythm waveform in the second series of sensor data to identify a coherence therebetween. The system may determine an amount of volition in the subject's body based on the coherence. The first and second sensor may also be attachable to a head and a body part of one or more additional subjects in a social group, respectively. The social group may include a social interaction group, a sports group or a ballet performance group. The system may use the same steps to determine the amount of volition in the one or more additional subjects in the social group. The system may also determine a diagnosis or a treatment plan for the subject based on the amount of volition and present the diagnosis or the treatment plan on a display.

In determining the amount of volition, the system may generate a first and second spectrograms from a pair of micro-rhythm waveforms. The system may compare the first and second spectrograms to generate a cross-spectrum coherence graph representing the coherence between the first and second micro-rhythm waveforms. The system may generate a phase angle graph representing phase angle values based on the cross-spectrum coherence graph. The system may determine whether a bodily activity associated with the first sensor is leading or lagging a bodily activity associated with the second sensor based on the polarity of the phase angle value.

DETAILED DESCRIPTION

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present solution may be embodied in other specific forms without departing from its spirit or essential characteristics. The described embodiments are to be considered in all respects only as illustrative and not restrictive. The scope of the present solution is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present solution should be or are in any single embodiment of the invention. Rather, language referring to the features and advantages is understood to mean that a specific feature, advantage, or characteristic described in connection with an embodiment is included in at least one embodiment of the present solution. Thus, discussions of the features and advantages, and similar language, throughout the specification may, but do not necessarily, refer to the same embodiment.

Furthermore, the described features, advantages and characteristics of the present solution may be combined in any suitable manner in one or more embodiments. One skilled in the relevant art will recognize, in light of the description herein, that the present solution can be practiced without one or more of the specific features or advantages of a particular embodiment. In other instances, additional features and advantages may be recognized in certain embodiments that may not be present in all embodiments of the present solution.

Reference throughout this specification to "one embodiment". "an embodiment", or similar language means that a particular feature, structure, or characteristic described in connection with the indicated embodiment is included in at least one embodiment of the present solution. Thus, the phrases "in one embodiment". "in an embodiment", and similar language throughout this specification may, but do not necessarily, all refer to the same embodiment.

As used in this document, the singular form "a," "an," and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to."

The present disclosure concerns systems and methods for connecting peripheral and central nerves output signatures of variability through the same statistical platform. The technical aspects of the present solution that are novel relative to existing technology or products include, but are not limited to: (1) the statistical platform that it is based on; (2) the decomposition of actions into levels of control with a corresponding decomposition of thought processes and decisions; and/or (3) an ability to accommodate dynamic inputs for variables measured in a stochastic way. These features of the present solution will become more evident as the discussion progresses.

The present solution discloses a statistical methodology to study brain-body interactions and connect signals from the intentional thoughts with signals from the physical activities. Both the peripheral and central networks of the nervous systems can now be studied under the same statistical framework as the framework permits real-time tracking of the statistical signal using non-invasive means. This framework permits the individualized profiling of the stochastic signatures characterizing the fluctuations in the person's nervous systems to track processes at all levels of control from autonomic to automatic to intentional. In particular, it is possible to objectively assess the degree of volitional control of the person in a given situation. This has implications for clinical areas, as well as for legal matters where volition/intent has to be dissociated from spontaneity.

The present solution can be used in a variety of applications. For example, the present solution can be used to: evaluate clinical trials (especially in therapeutic areas lacking objective and quantitative measurement of disease condition (e.g., neurodevelopmental diseases such as Autism, neurodegenerative diseases such as Parkinson's disease and Alzheimer's disease, coma, and/or pain)); track treatment effectiveness and risks; track sleep; assess and track sports and arts performance; assess and track motor learning across the central and peripheral networks; evaluate newborn babies' development; assist with pharmaceutical research; assist with skill development in sports, arts and body and mind coordinated activities; and/or assist with pediatrics and research. The present solution may also be used to track dyadic interactions in the clinical setting (e.g., when a clinician is administering a questionnaire to the person) or when two dancers perform a routing). The scope of the present solution is not limited to the nervous systems of one person. The methods can be extended to two or more individuals in a group so as to track social interactions.

Referring now to FIG. 1, there is illustrated an example of system 100. System 100 is a network-based system in which computing device 400 can be deployed in some scenarios. In this network-based scenario, computing device 400 is communicatively coupled to a server 160 and other computing devices $140_1, \ldots, 140_N$ via a network 150 (e.g., the Internet or Intranet). Computing devices $140_1, \ldots, 140_N$ can be the same as, similar to, or different than computing device 400. During operation, computing devices 400, $140_1, \ldots 140_N$ may write data to or read data from database 170. Each computing device 400, $140_1, \ldots, 140_N$ includes, but is not limited to, a robot, a three dimensional ("3D") animate, a personal computer, a laptop computer, a desktop computer, a personal digital assistant, a smartphone or any other electronic device having input and output components (e.g., a speaker, a display screen, a keypad and/or a touch screen). In some scenarios, the present solution includes software that is at least partially installed and run on the computing device 400, computing device $140_1, \ldots, 140_N$ and/or server 160. In some scenarios, system 100 may include sensors 102 and 104 that are attachable to a head a subject and sensors 106, 108, 110, 112, 114, 116, and 118 that are attachable to a body part of the subject. The system may communicate sensor data from sensors 102-118 to computing device 400 via network 130. In some scenarios, the communication is a real-time communication.

Figure 3:
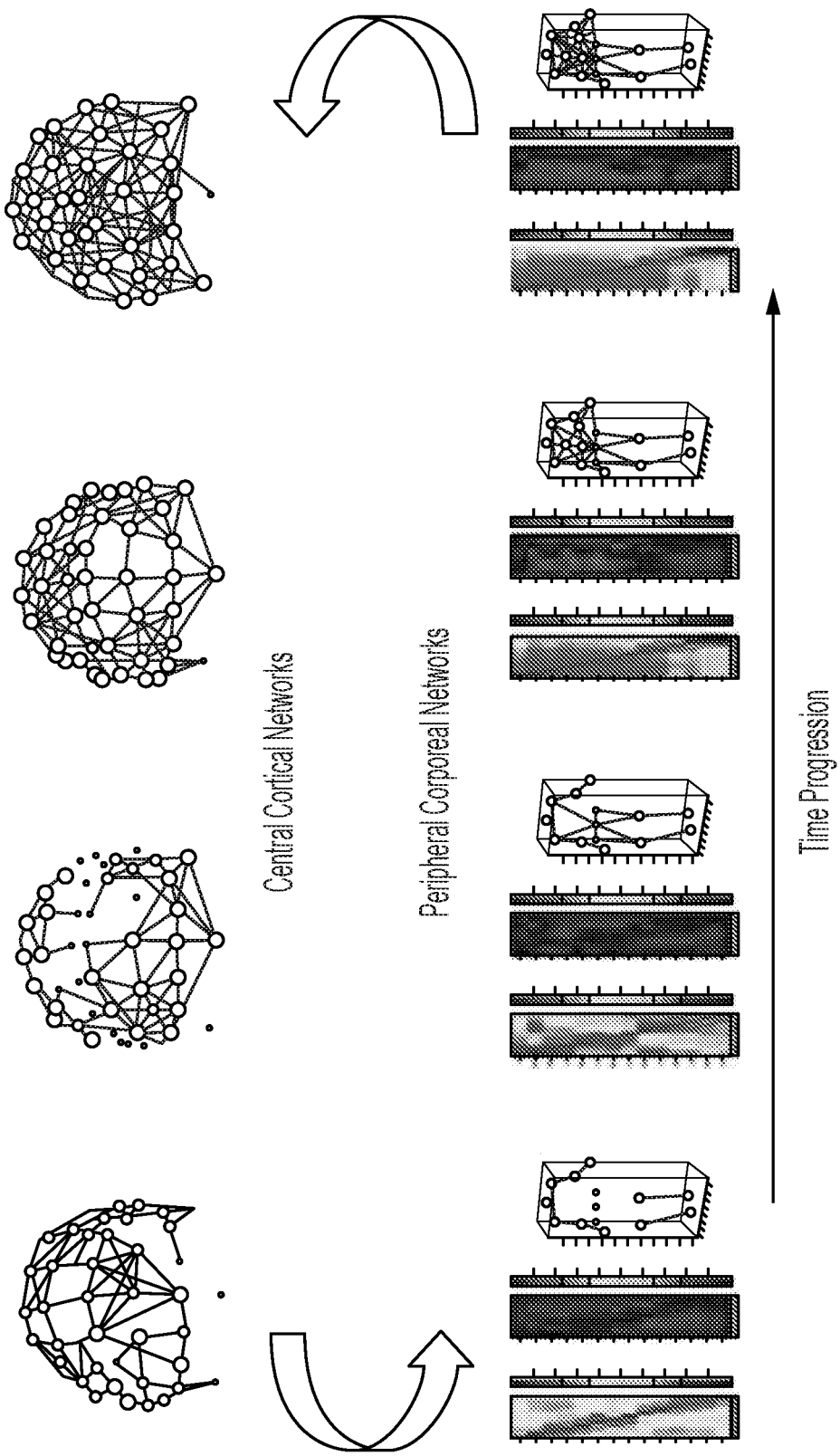
FIG. 3 illustrates an example of a statistical methodology used to study brain-body interactions and connect signals from the intentional thoughts with signals from the physical activities.

Referring now to FIG. 3, there is provided an illustration that is useful for understanding a statistical methodology to study brain-body interactions and to connect signals from a person's intentional thoughts with signals from the person's physical activities. During operation, brain-body network interactions are defined by patterns of synchronization across different nodes defined by a plurality of channels (e.g., 64 channels) registering electroencephalographic activities and outputs of sensors physically attached to a plurality of joints (e.g., 14 joints) of a person's body (e.g., head, shoulders, elbows, etc.).

In this example, a total of 78 nodes are considered. These nodes are linked to each other through different levels of strength that change the number of links to each node over time. The colors of the nodes reveal self-emerging modules, while their sizes reveal the degree of connectivity (number of incoming and outgoing links). The thickness of a link (or its absence) reflects the level of synchronization (from 0 absent to 1 full strength). The matrices show the bodily patterns as they unfold in time (left-hand side is the actual values, right-hand side is the binary values after using a threshold to explore and to determine levels of synchronization across a range of values of the threshold). These are existing methods of network connectivity analyses, but the present disclosure provides a statistical platform to connect both the brain and the body as well as to automatically identify self-emerging unfolding patterns. Further, the extension of the network analyses to the peripheral bodily grid of nodes provides the means to connect brain and body dynamics and unveil synergistic (coupled) dynamics under a common statistical platform.

The existing research in brain science has taken a disembodied approach to the tracking of cortical activity and the study of the intentional (mental) control of human behaviors. The physical bodies in motion are not considered in the research to capture their inherent signatures of variability oscillating between intentional and spontaneous states. On the other hand, the behavior is realized through the physical (volitional) control of human bodies in motion. Yet, the fields that study the neural control of movements do so without a proper framework that allows for the inclusion of abstract cognitive aspects of a human's mental life.

For example, in the brain domain, functional Magnetic Resonance Imaging ("fMRI") research must be done while the subject lies still trying hard not to move (as instructed). Any micro-motion below a certain threshold will be used as criteria to select the data to be included in the analyses. The rest of the data are discarded. Motor control paradigms, guided by computational models that predefine and constrain the time profiles of motions to targets, treat the movements falling largely beneath awareness and the unin-structed, goal-less movements as noise. The two fields of research remain disconnected. The data is handcrafted in a 'self-fulfilling prophesy' approach that will face many challenges when trying to adapt it to the realities that translational, clinical applications demand.

The present solution takes a different approach to the study of brain-body interactions and connects signals from the intentional thoughts with signals from their physical realization at will. The present solution provides a way to track the trajectories of the stochastic signatures of the variability of mental and bodily activities in tandem as the person interacts with the environment in a closed loop. Instead of treating motion fluctuations in the ElectroEn-cephaloGram ("EEG") data as a nuisance, smoothing it out through averaging and throwing them away as noise, the present solution characterizes their stochastic signatures. Likewise, instead of discarding goal-less, spontaneous movements beneath awareness, the present solution registers them and characterizes their sensory-motor signatures across naturalistic behaviors and contextual situations.

FIG. 3 shows an example of the first steps in the process of linking mental and bodily activities from the raw output data collected from various sensors. The top trajectory across the scalp contains the activation patterns of the network representing 64 sites (4 stages are shown for simplicity) as the nodes and links evolve in time. This graph is obtained by unfolding patterns of synchronicity across channels using traditional Phase Locking Value ("PLV") analyses to capture the changes in synchronous activation across the nodes. The same PLV analysis is performed across the bodily joints as they rotate and translate in space and time. In both cases, the activity value is filtered through various thresholds (from 0 to 1 whereby 0 is asynchronous, and 1 is fully synchronous) to explore various distributions reflecting degrees of synchronization across brain areas. This first step builds a binary adjacency matrix that can be used to extend the central network to the peripheral network so as to assess how brain areas synchronize and desynchronize with peripheral nodes (joints) over time. Further, other signal processing tools are used to carry out analyses in the frequency domain (e.g., cross-coherence analyses determining lead-lag phase angles and using weighted directed graphs to represent dynamically changing network states). All the machinery from network topology analyses can then be imported here to examine the brain and body in tandem as their statistics evolve along different time scales.

Central and peripheral activation profiles are connected using the same mathematical framework of network topology and the statistical approach borrowed from particle physics. Both (now joined) networks are characterized as one where stochastic processes of their inherent variability can be tracked. The level of noise-to-signal ratios across the nodes is automatically tracked in tandem with the evolution of the shape of the probability distributions of the micro-movements in the unfolding activity. The micro-movements, in this case, refer to random fluctuations in the amplitude of the normalized signal along the original timescale. This tandem tracking provides an ability to automatically know which areas are transmitting information between the mind and the body with maximal reliability, predictability, and bandwidth. This is in contrast to the current approaches that handpick the regions of interest to confirm a priori formulated hypotheses about brain regions involved in perceptual processes or imagined behaviors, in a disembodied fashion.

The binary un-weighted undirected network of FIG. 3 can also be converted into a weighted directed graph using the coherence values (weights signaling the strength of the links) and phase angle lead values (signaling the direction of activity from one node to another). That is, as the stochastic unfolding patterns change in tandem, self-emerging synchronous patterns emerge across the brain-body network. The stochastic signatures underlying these self-emerging synergies provide information about the degree of spontaneous randomness and noise across the network (the full central and peripheral network) as well as within each sub-network in the brain and the body. The dynamic transition from noise to well-structured and predictive signal across these inter-connected sub-networks can then be tracked over natural activities. This approach enables automatically detecting patterns and tracking their evolution by adopting and utilizing the same statistical distributional analyses that we have been using up to now adapted from particle physics. Here, power law distributions of the full network are uncovered, as well as topological features that necessarily guide the types of predictions about a person's nervous system's responses as compared to that of others performing the same or similar actions.

The present formulation of the central-peripheral networks can be extended to the social environment by treating the other individual's bodily and mental motions as another form of afferent sensory input to our nervous system and tracking the influences of that peripheral signal on our central control of actions and thoughts.

To illustrate this application, it is assumed the present solution is used in the context of dyadic and triadic interactions during one of the main diagnostics tools in autism, such as the ADOS-2 in Lord, C., et al., Autism diagnostic observation schedule. 2012: Western Psychological Services Torrance, Calif. In this standardized setting, there is an examiner and an examinee and often a parental interaction with one another. At any given time, when taken as a full network, the levels of entrainment and/or de-synchronization of the dyad or triad are known as the behavior unfolds. Using the abovementioned tools, these features of natural interactions can be tracked as they unfold in time.

Likewise, in therapeutic settings (e.g., in hippotherapy and occupational therapy), the therapist, the child, and the horse are recorded as they interact in real time during the therapy. This enables a characterization of the sensory-motor patterns underlying the participants' network's interactions. In these cases, outcome measures can be obtained to provide insurance companies with the proper evidence to assess effectiveness, risk, and generalization so as to be able to claim coverage for the patients' families.

In FIG. 1, in some scenarios, the system may include a first sensor (e.g., sensors 102 and 104 of FIG. 1) attachable to a head of a subject and configured to measure a rhythm of the subject over a recording time and generate a first series of sensor data of the subject. The first series of sensor data may include one or more micro-rhythm waveforms. The system may also include a second sensor (e.g., sensors 106, 108, 110, 112, 114, 116, and 118 of FIG. 1) attachable to a body part of the subject and configured to measure a rhythm of the subject over a recording time and generate a second series of sensor data of the subject. The second series of sensor data may include one or more micro-rhythm waveforms. The first sensor may include an EEG device having one or more electrodes. The second sensor can be an accelerometer, a gyroscope, a motion sensor, a vibration sensor, a position sensor, a restoration sensor, an electromyography sensor, an electrocardiogram sensor, a RIP sensor, or an MRI sensor. The second sensor may be attached to a hand, a foot, a leg, a chest, a waist, an arm, or ankle of the subject.

In some scenarios, the system may perform a power spectral analysis of a first micro-rhythm waveform in the first series of sensor data and a second micro-rhythm waveform in the second series of sensor data to identify a coherence therebetween. The system may determine an amount of volition in the subject's body based on the coherence. In some scenarios, the first and second sensor may further be attachable to a head and a body part of one or more additional subjects in a social group, respectively. The system may determine the amount of volition in the one or more additional subjects in the social group. The social group can be a social interaction group, a sports group or a ballet performance group. In some scenarios, the system may also determine a diagnosis or a treatment plan for the subject based on the amount of volition and output the diagnosis or the treatment plan on a display.

Before performing the power spectral analysis, the system may normalize one or more micro-rhythm waveforms in the first and second series of sensor data to generate a corresponding normalized micro-rhythm waveform. The normalized micro-rhythm waveform may be unitless and scaled from zero to one.

For the micro-rhythm waveform derived from each electrode of the EEG device, the system may also determine a Noise-to-Signal Ratio ("NSR") over the recording time for each of the one or more micro-rhythm waveforms. They system may re-reference each of the micro-rhythm waveforms by subtracting therefrom an NSR corresponding to a sensor having a lowest average NSR over the recording time among all of the one or more micro-rhythm waveforms in the first and second series of sensor data. In determining the NSR for each of the one or more micro-rhythm waveforms, the system may estimate moments of a continuous family of a probability distribution function for each of the one or more micro-rhythm waveforms in the first and second series of sensor data, and use the estimated moments to determine the NSR. In some scenarios, the probability distribution function is a Gamma function, a Gaussian distribution function, or a lognormal distribution function. In some scenarios, the estimated moments of the probability distribution function may include an estimated scale parameter of the Gamma function.

In determining the amount of volition, the system may generate a first spectrogram from the first micro-rhythm waveform and a second spectrogram from the second micro-rhythm waveform. The system may further compare the first spectrogram and the second spectrogram to generate a cross-spectrum coherence graph representing the coherence between the first and second micro-rhythm waveforms. The cross-spectrum coherence graph may include a plurality of peaks along a frequency axis, each of which indicates a frequency at which the first micro-rhythm waveform and the second micro-rhythm waveform are coherent. The system may further generate a phase angle graph representing phase angle values along the frequency axis. For each two successive peaks in the cross-spectrum coherence graph, the system may identify a synchronous pattern between the two successive peaks. The system may determine a polarity of a phase angle value between two frequencies where each of the two successive peaks are located, and determine whether a bodily activity associated with the first sensor is leading or lagging a bodily activity associated with the second sensor based on the polarity of the phase angle value.

In some scenarios, the system may further generate a network including a plurality of nodes and a plurality of links. Each node in the network represents a sensor coupled to the subject, and each link connects between a first and second node, the link representing a module between bodily activities measured by a sensor associated with the first node and bodily activities measured by a sensor associated with the second node. In some scenarios, the system may further generate a multi-dimensional graphical representation for the network, in which each node is represented by a circle. A color of the circle represents a coherence value along a color bar, and a size of the circle represents a number of links passing through the node represented by the circle. The representation scheme used in the present example is for illustration purposes only. Other forms of visualization for the network are possible.

The term "module" refers to a self-emerging sub-network within the network whereby the degree connectivity within the subnet is maximal, and the degree connectivity between the subnet and the rest of the network is minimal. Tracking the modules minute by minute permits tracking double connections of the coupled brain-body networks. This means that links in a body region point to a node in a brain region and links in the brain region point back to that node in the body region.

Figure 2A:
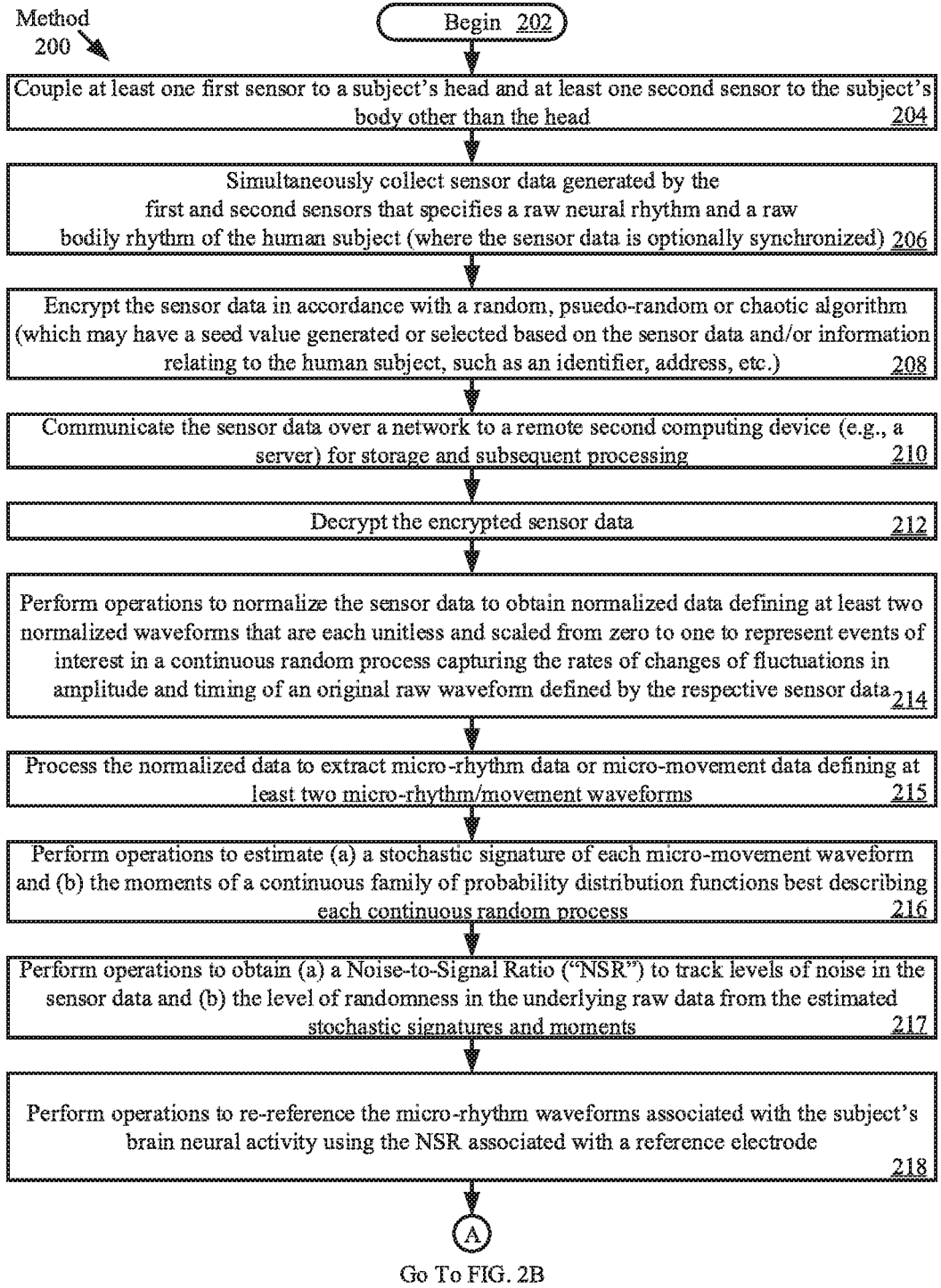
FIGS. 2A-2C (collectively referred to as "FIG. 2") illustrate a flow diagram of (a) an example of a method for detecting and analyzing a neurological disorder in a human subject and (b) an example of a method for data compression.

Referring now to FIG. 2A, the above-illustrated system is described in detail. A method 200 that can be implemented in the above illustrated system for detecting and analyzing a neurological disorder in a human or animal subject may couple at least one sensor (e.g., sensor 450 of FIG. 4, and/or sensors 102-118 of FIG. 1) to the human or animal subject for obtaining data from at least one physiological relevant signal 204. The system may also couple at least one first sensor (e.g., sensors 102 and 104 of FIG. 1) to the subject's head, and couple at least one second sensor (e.g., sensors 106, 108, 110, 112, 114, 116, and 118 of FIG. 1) to a part of the subject's body other than the subject's head (e.g., arm, chest waist, leg, hand, foot). The first sensor can include but is not limited to, an EEG sensor. The second sensor can include, but is not limited to, an accelerometer, a gyroscope, a motion sensor, a vibration sensor, a position sensor, a restoration sensor, and/or a medical sensor (e.g., an electromyography sensor, an electrocardiogram sensor, an RIP sensor, an MRI sensor, etc.). An illustration of a plurality of sensors coupled to a person's head and body are shown in FIGS.

This system may simultaneously or concurrently collect sensor data measured by the first and second sensor 206. In this step, the system may also involve operations to synchronize the sensor data (e.g., for placing all of the sensor data in the same time domain format and/or for removing artifacts therefrom). In some scenarios, the synchronization of multiple sensors from different equipment is achieved through the public platform LabStreamLayer. The system may use a user interface to monitor data acquisition over Wi-Fi network streaming the data from the multiple wireless sensors. Time stamping data buffering and disk writing from all sensor equipment with millisecond time precision enables the time alignment of all data streams.

In some scenarios, the sensor data generated by the first sensor specifies raw neural (cortical surface) rhythm. The neural rhythm defines activity in a subject's brain and/or CNS. The sensor data generated by the second sensor(s) specify a neural rhythm (read out from the skin surface) and reflect the flow of information from bodily peripheral nerves created in part by the human or animal subject's physiological (e.g., nervous) system. For example, in some scenarios, the sensor data generated by the second sensor(s) relates to kinematics motion parameters continuously registered as a time series of changes in signals generated by the human or animal subject's nervous system. The raw bodily rhythm can include but is not limited to, voluntary bodily rhythms, involuntary bodily rhythms, and autonomic bodily rhythms. For example, the raw bodily rhythm defines respiratory rhythms, muscle rhythms and/or heartbeat rhythms. The system may obtain the sensor data from a variety of medical tests, an EEG test, a fMRI test, an MRI test, an ECG test, and/or a RIP test.

Figure 5A:
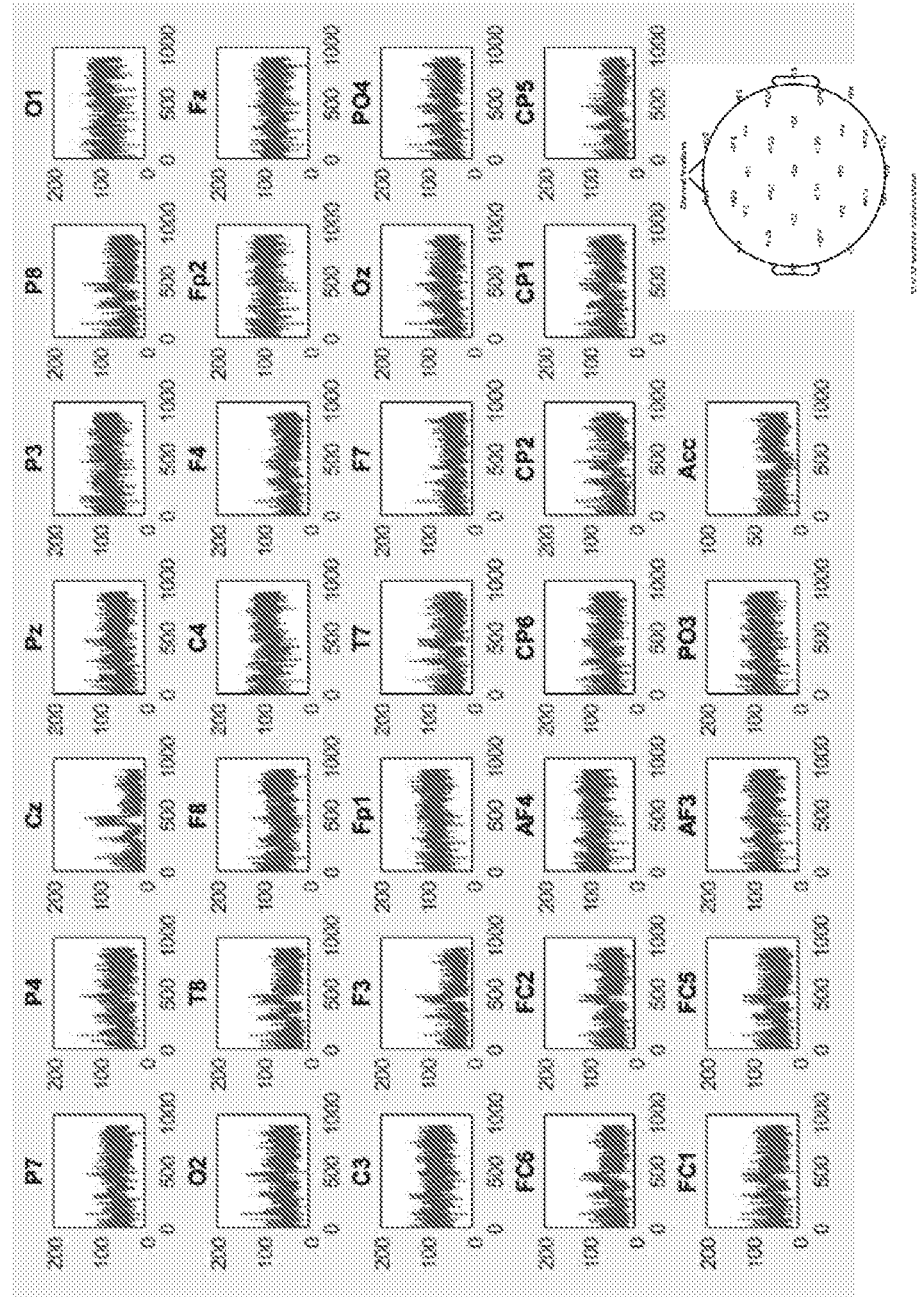
FIGS. 5A-5B (collectively referred to as "FIG. 5") illustrate an example of sensor data generated by sensors coupled to a human subject's body.
Figure 5B:
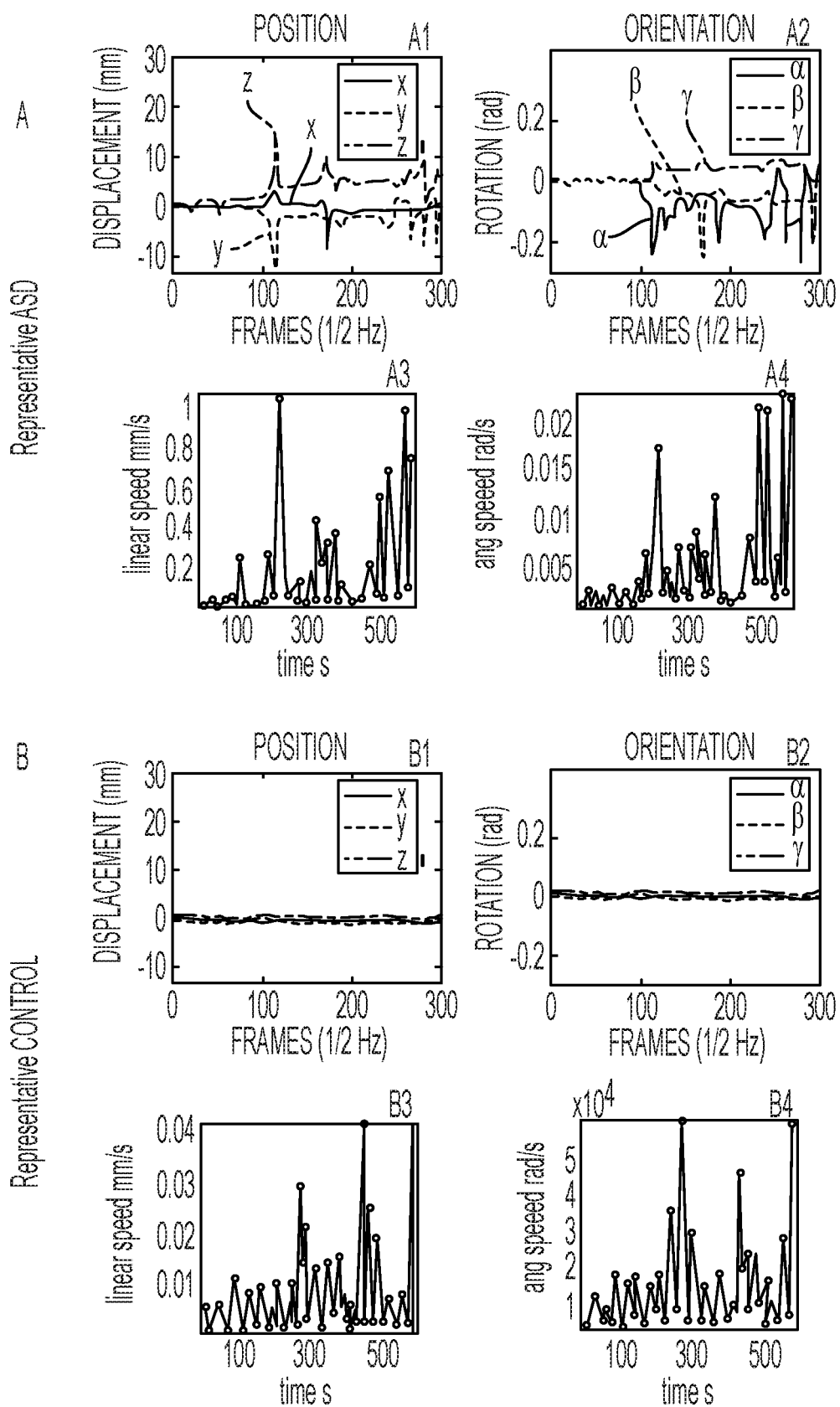

Graphs plotting an example of sensor data generated by the first sensor are provided in FIG. 5A and sensor data generated by the second sensor is provided in FIG. 5B. In FIG. 5A, the first sensor data includes samples of raw brain neural activity extracted from EEG data generated using thirty-two (32) electrodes disposed at a plurality of locations P7, P4, Cz, Pz, P3, P8, O1, O2, T8, F8, C4, F4, Fp2, Fz, C3, F3, Fp1, T7, F7, )z, PO4, FC6, FC2, AF4, CP6, CP2, CP1, CP5, FC1, FC5, AF3, PO3 on the subject's head.

In FIG. 5B, the second sensor data includes samples of raw head motions extracted from Resting-State fMRI ("RS-fMRI") data, as shown by graphs A1, A2, B1, and B2. The system may extract displacement and rotation kinematics from raw sensor data using a Statistical Parametric Mapping ("SPM8") method from raw RS image files. The image files may be obtained from a database (e.g., such as an Autism Brain Imaging Data Exchange ("ABIDE") database). The image files may have a Neuroimaging Informatics Technology Initiative ("NifTI") format. This extraction yielded three (3) positional parameters and three (3) orientation parameters. Graphs A1 and A2 plot representative ASD participant's linear displacements and angular rotations of the subject's head registered with respect the first frame. Graphs B1 and B2 plot representative control subject's linear displacements and angular rotations of the subject's head registered with respect the first frame.

The second sensor data also includes data defining speed profiles, as shown by graphs A3, A4, B3, and B4. The system may also obtain speed profiles by computing a Euclidean norm of each three-dimensional velocity vector (Δx, Δy·Δz) displacement at each point of application (x, y, z) from frame to frame. For example, for three hundred (300) frames, a speed profile is defined by the following mathematical equation (1).

$$\text{speed}_{frame} = \sqrt{(\Delta x)^2 + (\Delta y)^2 + (\Delta z)^2} \tag{1}$$

To obtain velocity vector fields with corresponding speed scalar temporal profiles, the system may analyze the position data using different methods and the results compared. For example, the system may filter position data using a triangular filter to preserve the original temporal dynamics of the first rate of change data (i.e., the original timing of the peaks) while smoothing the sharp transitions from frame to frame (using triangular window $$v'(i) = \frac{\sum_{k=-d}^{d} (v(k+i) \cdot (d+1-|k|))}{\sum_{k=-d}^{d} (d+1-|k|)}$$

for velocity v of frame i, k summation index from −d to d and testing various values of d. e.g., up to 6, to build a symmetrically weighted sum around the center point, frame by frame.

Figure 6:
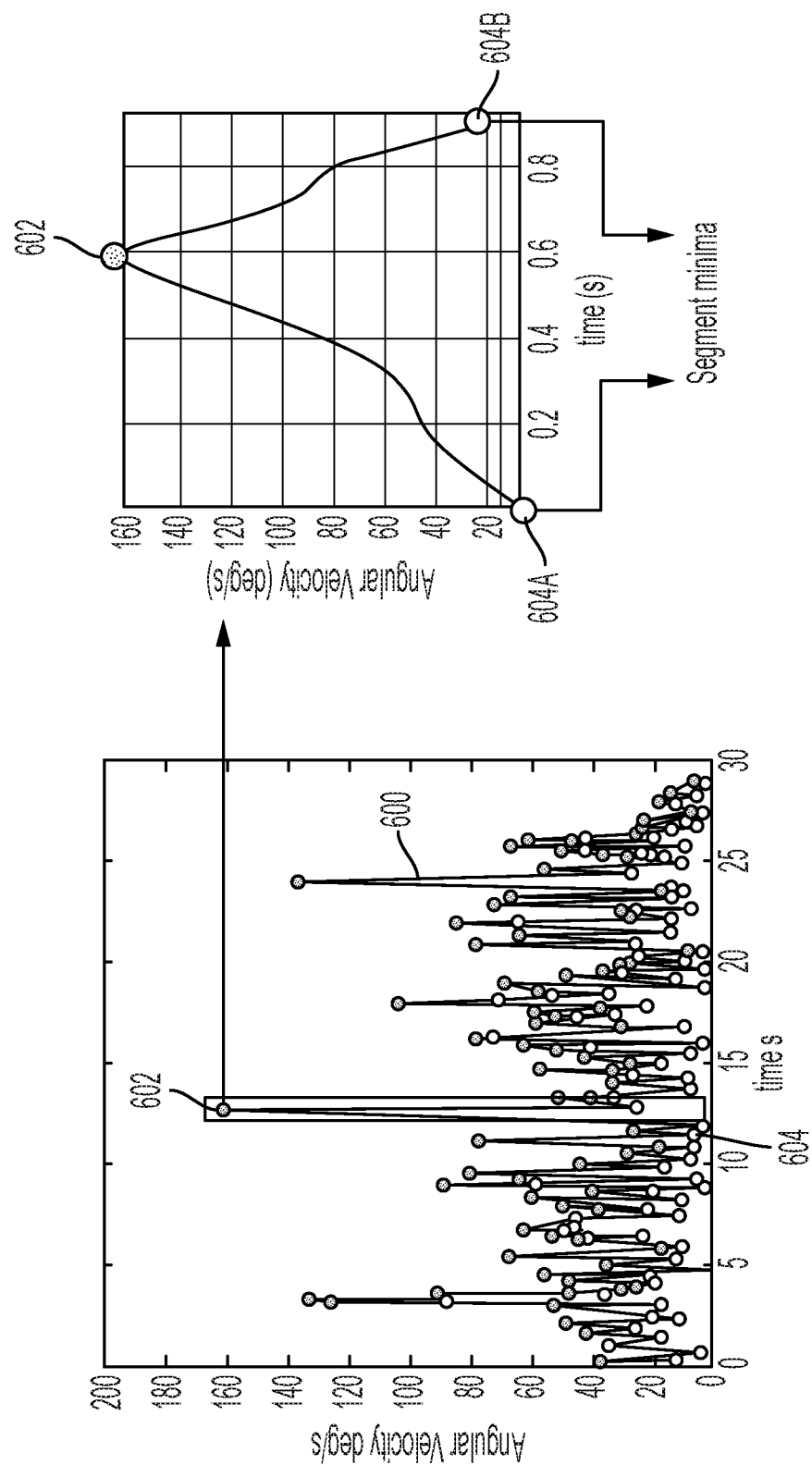
FIG. 6 illustrates an example of sensor data and normalization procedure.

In FIG. 6, the sensor data may include data defining the rate of change of a hand's rotation. As such, the x-axis represents time, and the y-axis represents angular velocity. Accordingly, the scale of the graph's x-axis is in seconds, and the scale of the graph's y-axis is in degrees per second. The plotted data points for angular velocity define an original raw waveform 600. Waveform 600 includes a plurality of peaks 602 and a plurality of valleys 604. Each peak 602 is defined by a data point at which the waveform's slope changes from a positive slope to a negative slope. In contrast, each valley 604 is defined by a data point at which the waveform's slope changes from a negative slope to a positive slope.

Referring to FIG. 2A, once the sensor data has been collected, the first computing device may optionally encrypt the same so as to comply with at least the Health Insurance Portability and Accountability Act ("HIPAA") confidentiality requirements 208. The system may encrypt the sensor data using a chaotic, random or pseudo-random number based algorithm, or any suitable chaotic, random or pseudo-random number based algorithm, known or later developed. A seed value for the chaotic, random or pseudo-random number based algorithm can be selected from a plurality of pre-defined seed values or dynamically generated during operations of the first computing device. The term "seed value," as used herein, refers to a starting value for generating a sequence of chaotic, random, or pseudo-random integer values. The system may select or generate seed value(s) based on the sensor data and/or information relating to the human or animal subject (e.g., an identifier, an address, a phone number, an age, a medical diagnosis, a medical symptom, information contained in a medical history, a stochastic signature value, a noise signal ratio value, a moment value, any other value determined in a previous iteration of method 200, etc.).

Optionally, the system may communicate the sensor data to a remote second computing device 210 (e.g., computing device $140_1, \ldots 140_N$ or server 160 of FIG. 1) over a network (e.g., network 130 and 150 of FIG. 1), for storage in a data store (e.g., memory 408 of FIG. 4 or database 170 of FIG. 1) and subsequent processing. In some scenarios, the system may decrypt the sensor data 212 if it was previously encrypted. Any suitable known or to be known decryption technique can be used herein without limitation.

In some scenarios, the system may perform operations to normalize the sensor data 214. This step is useful when dealing with parameters of different units and scales. The normalized data define a plurality of normalized waveforms that are unitless and scaled from zero (0) to one (1). In some scenarios, forty-three (43) normalized waveforms are obtained. Thirty-two (32) of the normalized waveforms correspond to the thirty-two (32) EEG electronics disposed on the human subject's head (e.g., as shown in FIG. 5A), and eleven (11) of the normalized waveforms correspond to the eleven (11) sensors disposed on body parts other than the head (e.g., the chest, waist, upper left arm, upper right arm, left wrist, right wrist, left ankle, right ankle, left foot, right foot, back of the neck, and lower back as shown by the square boxes in FIG. 1).

Each normalized waveform represents events of interest in a continuous random process capturing rates of changes in fluctuations in amplitude and timing of an original raw waveform (e.g., waveform 600 of FIG. 6 for sensor data generated by a second sensor) generated by the respective sensor data (e.g., sensor data 600 of FIG. 6). Any suitable known or to be known data normalizing method can be used herein without limitation.

In more general terms, the system may perform normalization to standardize the different resolutions and/or scales/units of the time series waveforms generated by the sensor data. For example, a heart rate waveform has a millisecond scale. A velocity waveform has a centimeter per second scale. An acceleration waveform has a meter per second squared scale. The different units of these waveforms are standardized in a waveform which is normalized from zero (0) to one (1).

In some scenarios, the system may perform the sensor data normalization using the Euclidean distance so that all parameters have the same scale. The following mathematical equation (2) is used to implement a unity-based normalization.

$$X_{i,0\,to\,1} = \frac{X_i - X_{Min}}{X_{Max} - X_{Min}} \quad (2)$$

where $X_i$ represents each data point i, $X_{MIN}$ represents the minima among all the data points, $X_{MAX}$ represents the maxima among all the data points. $X_{i,\,0\,to\,1}$ represents the data point i normalization between zero (0) and one (1). Alternatively, the following mathematical equation (3) can be used to produce a set of normalized data with zero (0) being the central point.

$$X_{i,-1\,to\,1} = \frac{X_i - \left(\frac{X_{Max} + X_{Min}}{2}\right)}{\left(\frac{X_{Max} - X_{Min}}{2}\right)} \quad (3)$$

where $X_i$ represents each data point i, $X_{MIN}$ represents the minima among all the data points, $X_{MAX}$ represents the maxima among all the data points, $X_{i,\,-i\,to\,1}$ represents the data point i normalization between zero (0) and one (1).

In other scenarios, the system may perform the sensor data normalization using the following mathematical equation (4).

$$NormPVIndex = \frac{SpeedMax}{SpeedMax + AvrgSpeed} \quad (4)$$

where NormPVIndex represents a normalized data point, SpeedMax represents a value of a peak (e.g., peak 602 of FIG. 6), and AvrgSpeed represents an average of all data point value between a first valley (e.g., valley 604A of FIG. 6) immediately preceding the peak and a second valley (e.g., valley 604B of FIG. 6) immediately following the peak.

Figure 7A:
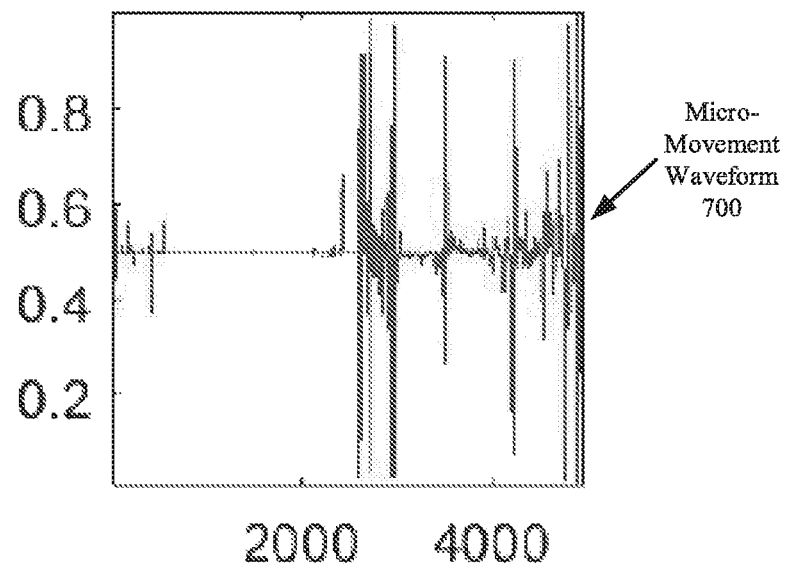
FIGS. 7A-7B (collectively referred to as "FIG. 7") each illustrates an example of a micro-movement waveform extracted from raw movement data.
Figure 7B:
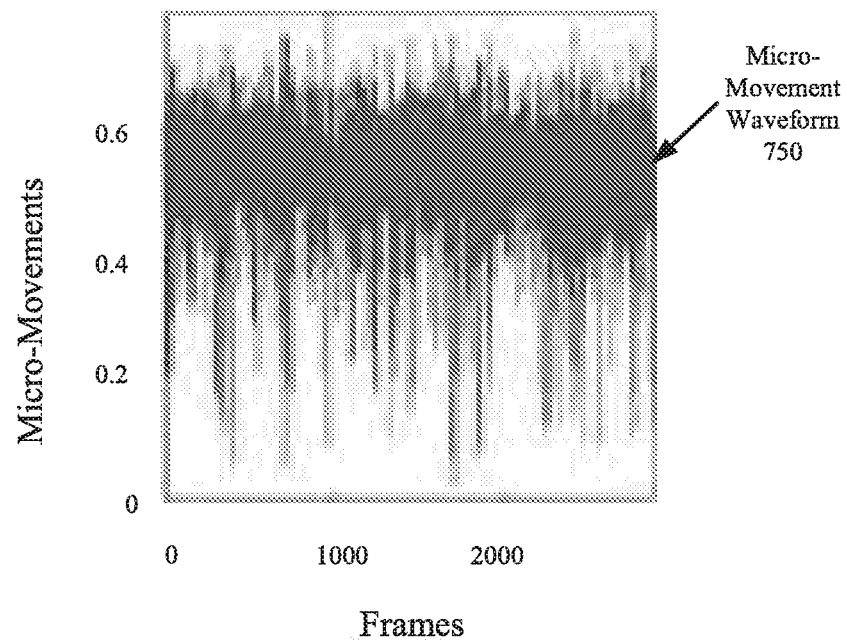

The system may process the normalized data to extract micro-rhythm data or micro-movement data defining a micro-rhythm or movement waveform 215. The terms "micro-rhythm data" and "micro-movement data," as used herein, refer to normalized data points (e.g., NormPVIndex$_1$, . . . , NormPVIndex$_N$). For example, a micro-movement data point constitutes a single normalized data point (e.g., the value of NormPVIndex$_1$). The micro-movement data defines a micro-movement waveform. An example of a micro-movement waveform 700 for a first sensor is shown in FIG. 7A and a micro-movement waveform 750 for a second sensor is shown in FIG. 7B.

Referring to FIG. 2A, the system may estimate (a) a stochastic signature of each micro-movement waveform and (b) moments of a continuous family of probability distribution functions best describing each continuous random process. The probability distribution function may be a Gamma function, a Gaussian Distribution function, and/or a Log-Normal Distribution function. Any suitable known Gamma, Gaussian Distribution and/or Log-Normal Distribution function can be used herein without limitation.

In some scenarios, the system may obtain each stochastic signature estimation by: performing statistical data binning using the respective micro-movement data; processing the respective binned micro-movement data to generate a frequency histogram; and performing a Maximum Likelihood Estimation ("MLE") process using the respective frequency histogram to obtain the respective stochastic signature.

Techniques for statistical data binning are known in the art. In some scenarios, in data binning, the system may group each set of micro-movement data points in respective bins, where micro-movement data points of each set have the same value (e.g., 0.1, 0.2, 0.3, 0.4, 0.5, 0.6, 0.7, 0.8, 0.9 or 1.0) or fall within a specified range of values (e.g., 0.0-0.1, 0.1-0.2, 0.2-0.3, 0.3-0.4, . . . , 0.9-1.0).

The system may use the binned data to generate a frequency table specifying the frequency of micro-movement data points in each bin (or stated differently, the total number of micro-movement data points in each bin). An example frequency table is shown below.

| 0.1 | 0.2 | 0.3 | 0.4 | 0.5 | 0.6 | 0.7 | 0.8 | 0.9 | 1.0 |
|---|---|---|---|---|---|---|---|---|---|
| 4 | 7 | 14 | 14 | 11 | 9 | 11 | 8 | 8 | 6 |

Figure 8:
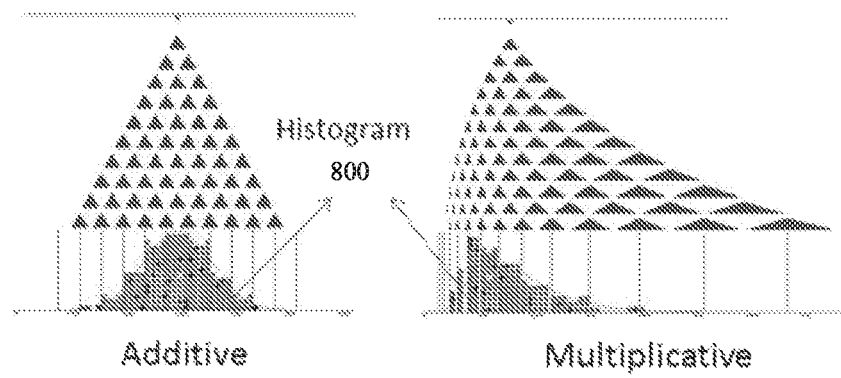
FIG. 8 illustrates an example of a histogram representative of a multiplicative random process.

The system may construct the frequency histogram from the frequency table. The intervals from the frequency table are placed on the x-axis, and the values needed for the frequencies are represented on the y-axis. In effect, the vertical columns of the frequency histogram show how many micro-movement data points are contained in each bin. An example of frequency histogram 800 is provided in FIG. 8.

The system may then use the frequency histogram in the MLE process to obtain an estimated stochastic signature. The MLE process includes estimating a mean value and a variance value while only knowing a relatively small number of sensed micro-rhythms or micro-movements of the human or animal subject. The MLE process accomplishes this by: generating probability distribution function waveforms using different sets of parameter values for known probability distributions (e.g., Gaussian, Gamma, Weibull, Log-Normal, etc.); and comparing the theoretical probability distribution function waveforms to the empirically generated frequency histogram (from the micro-movements data derived from the sensors (e.g., FIG. 7)) to identify the theoretical probability distribution function waveform that most closely matches the shape of the empirical frequency histogram. These empirically estimated parameters are then plotted in a parameter space with 95% confidence intervals. The system may use the estimated parameters to generate various indexes to facilitate statistical inference and interpretation of the results from data analyses.

In some scenarios, the system may use a Gamma function to generate the probability distribution function waveforms. The Gamma function is defined by the following mathematical equation (5).

$$y = f(x \mid a, b) = \frac{1}{b^{*}\Gamma(a)} x^{a-1} e^{\frac{-x}{b}} \quad (5)$$

where a is the shape parameter, b is the scale parameter, and y is the Gamma function result. Different sets of values for a and b are used to generate a plurality of Gamma function waveforms which are compared to the frequency histogram. The a and b values associated with the Gamma function waveform that most closely matches the shape of the frequency histogram define the stochastic signature for the human or animal subject.

Figure 9:
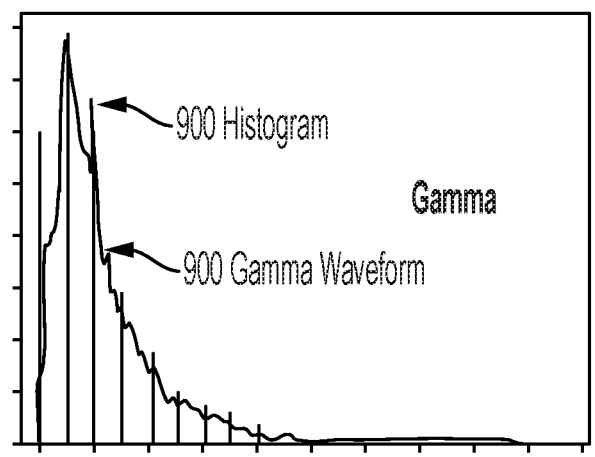
FIG. 9 illustrates an example of a Gamma function waveform.

An example of a Gamma function waveform 900 generated using mathematical equation (5) is shown in FIG. 9. The Gamma function waveform 900 is overlaid on top of the histogram 900 of FIG. 9. As can be seen from FIG. 9, the shape of Gamma function waveform 900 closely matches the shape of histogram 800. As such, the a and b values used as inputs to mathematical equation (5) define the stochastic signature for the human or animal subject.

Referring to FIG. 2A, the system may estimate the moments of a continuous family of probability distribution functions best describing the continuous random process 216. In the Gamma function scenarios, two moments are estimated. A first estimated moment includes a mean value μ defined by the following mathematical equation (6).

$$\mu = a \times b \quad (6)$$

A second estimated moment includes a variance value defined by the following mathematical equation (7).

$$\sigma = a \times b^2 \quad (7)$$

Referring again to FIG. 2A, the system may also perform operations to obtain (a) an NSR to track levels of noise in the sensor data and (b) a level of randomness in the underlying raw data from the estimated stochastic signature and/or moments 217. The NSR is defined by the following mathematical equation (8).

$$NSR = \sigma/\mu \quad (8)$$

In the Gamma scenarios, the above mathematical equation (8) can be re-written as the following mathematical equation (9).

$$NSR = (a \times b^2)/(a \times b) = b \quad (9)$$

As evident from mathematical equation (9), the NSR is equal to the scale parameter b in the Gamma scenarios. The level of randomness $L_{random}$ is derived in the gamma case from the fact that a=1 is the special case of the (memoryless) Exponential distribution (the most random distribution). As such, the closeness to a=1 is used as one criterion to determine randomness level. Other criteria may also be used based on indexes that show differences between the empirically estimated histogram and the exponential distribution fit to it.

In some scenarios, where an EEG sensor is used, the system may perform operations to re-reference the micro-rhythm waveforms associated with the subject's brain neural activity using the average NSR of each electrode across the entire recording time (minute by minute) and choosing the electrode with the lowest NSR on average. This electrode is then used as the reference electrode (e.g., electrode Cz is shown in FIG. 5A which has the average NSR across the electrode data). This re-referencing is achieved by subtracting the NSR signal from the micro-rhythm waveforms associated with the other electrodes (e.g., electrodes P7, P4, Pz, P3, P8, O1, O2, T8, F8, C4, F4, Fp2, Fz, C3, F3, Fp1, T7, F7, PO4, FC6, FC2, AF4, CP6, CP2, CP1, CP5, FC1, FC5, AF3, PO3 shown in FIG. 5A).

Figure 2B:
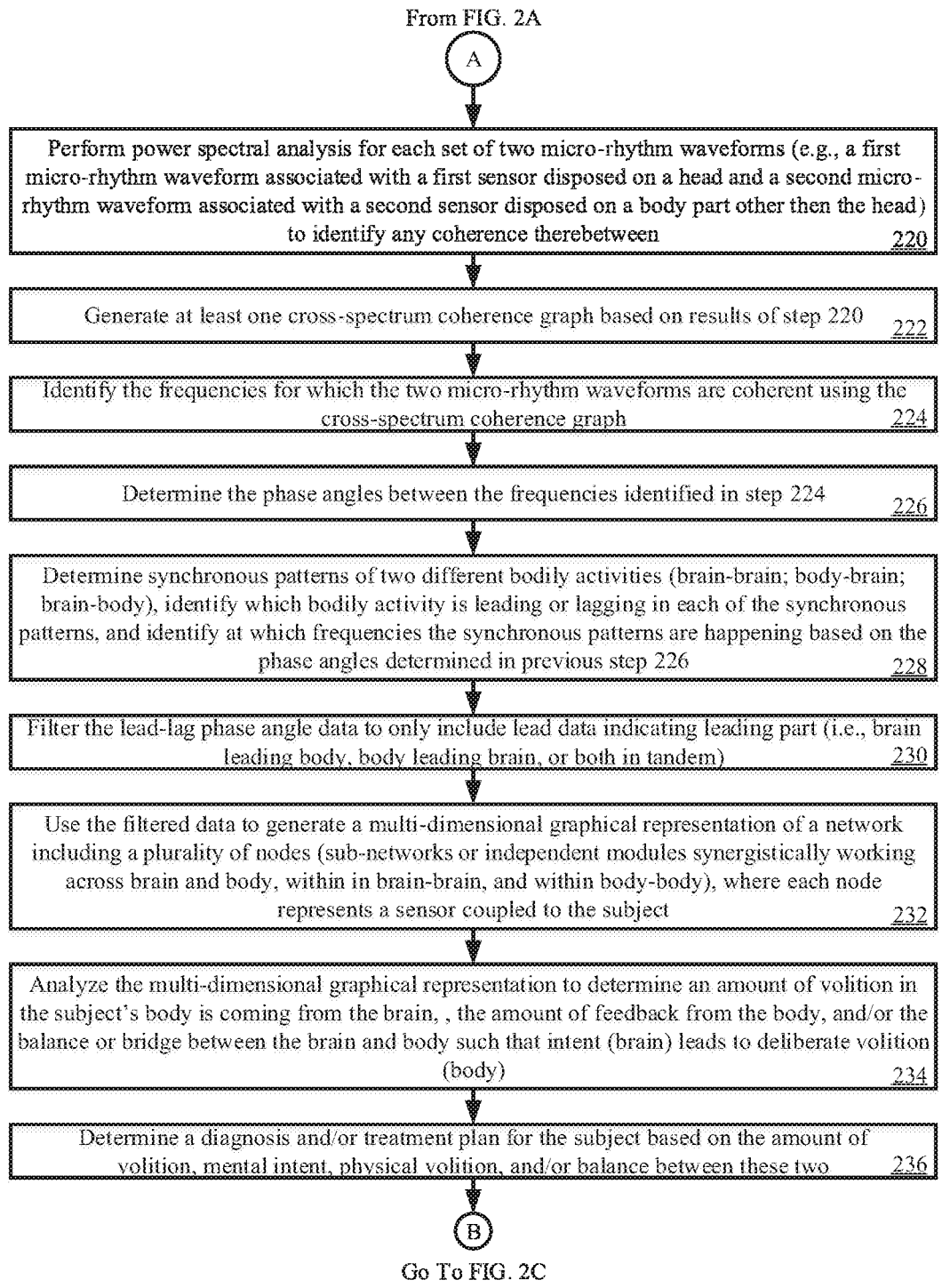

In FIG. 2B, the system may process the micro-rhythm waveforms. More specifically, the system may analyze each set of two micro-rhythm waveforms to identify any coherence therebetween 220. This identification can be achieved using power spectral analysis. In power spectral analysis, the system may generate a graph called a spectrogram (e.g., spectrograms 1010 and 1020 of FIG. 10) showing the power spectral density depicting the distribution of signal content over frequency.

In some scenarios, the system may analyze the following two (2) waveforms in a first iteration the signal analysis: a first micro-rhythm waveform associated with a first sensor (e.g., an EEG sensor) disposed on the subject's head; and a second micro-rhythm waveform associated with a second sensor (e.g., an accelerometer or other EEG sensor) disposed on a body part or the subject's head. The system may perform pairwise comparisons using well-known synchronicity metrics (e.g., cross-coherence, cross-correlation, phase locking value, etc.) by using a N×N matrix where N is the total number of sensors including EEG and body sensors.

The present solution is not limited to the particulars of this example. In some scenarios, the system may use sensors across the head and bodies of two or more people to study entrainment and synergistic patterns across multiple networks (e.g., social interactions; sports; ballet performance).

Figure 10:
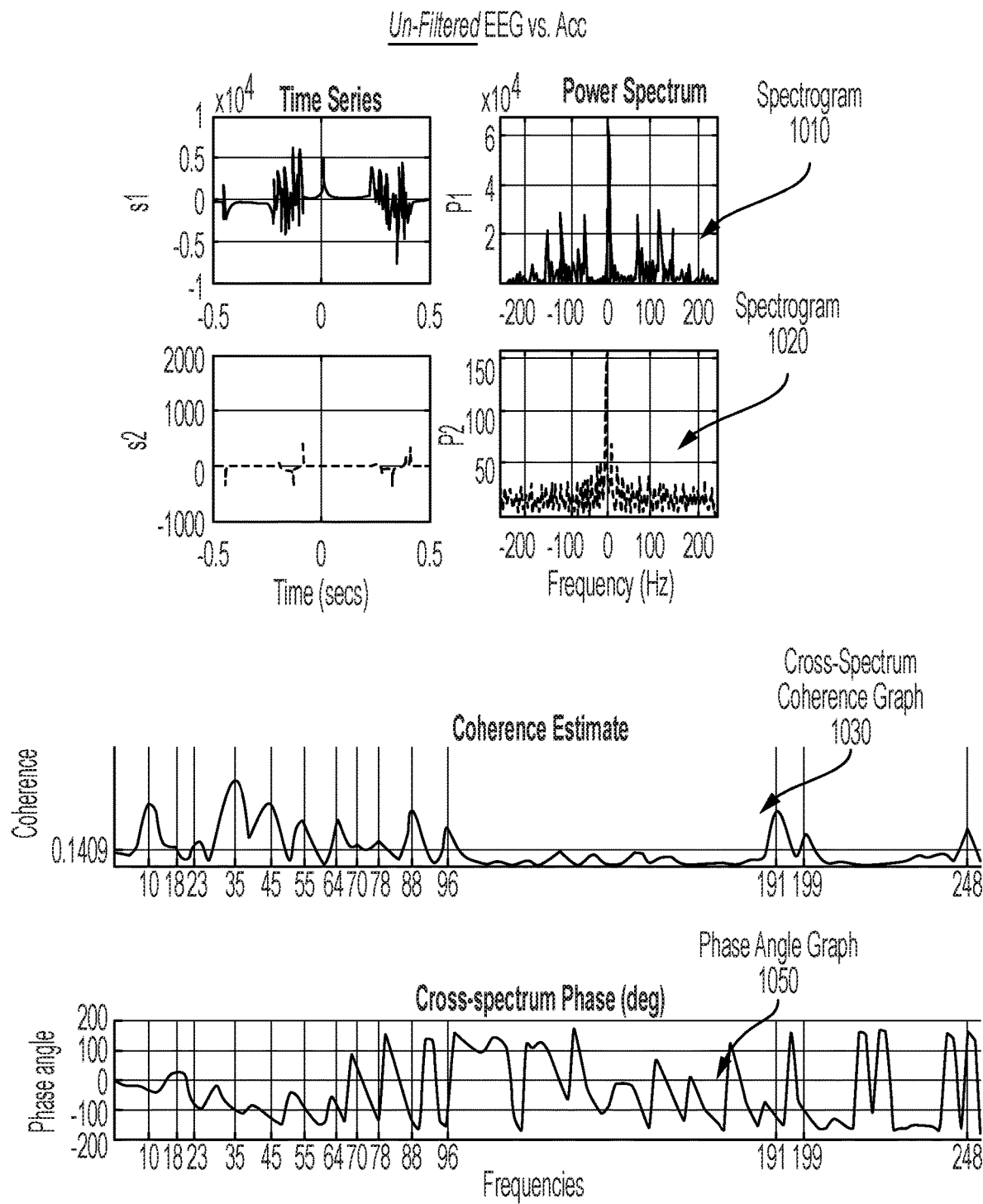
FIG. 10 illustrates an example of spectrograms, a cross-spectrum coherence graph, and a phase angle graph.

The system may generate at least one cross-spectrum coherence graph based on the spectrogram 222. This graph shows the frequencies at which there is high coherence between the signals from the two sensors (top panel of the coherence estimate figure) and the phase angle at which the coherence occurs for each frequency. Lead values are positive, and lag values are negative (bottom panel). An example of a cross-spectrum coherence graph 1030 is shown in FIG. 10.

The system may also analyze the cross-spectrum coherence graph to identify the frequencies for which the two micro-rhythm waveforms are coherent 224. The system may identify these frequencies as the frequencies at which a peak occurs in the cross-spectrum coherence graph. An example of a frequency graph 1050 is shown in FIG. 10. As shown in FIG. 10, a first peak exists in the cross-spectrum coherence graph 1050 between frequencies 10-18 Hz. A second peak exists in the cross-spectrum coherence graph 1050 between frequencies 23-35 Hz., and so on. The present solution is not limited to the particulars of FIG. 10.

With further reference to FIG. 2B, the system may determine the phase angles between adjacent peak frequencies 226. The system may then plot the phase angles on a graph. An example of a phase angle graph 1050 is shown in FIG. 10. The system may use the phase angle graph to determine synchronous patterns of two different bodily activities 228 (e.g., brain-brain, brain-body, body-body). In this step, the system may also identify which bodily activity is leading or lagging in each synchronous pattern, and determine what frequencies are the synchronous patterns happening. A positive angle indicates that a particular bodily activity (e.g., brain neural activity) is leading another particular bodily activity (e.g., hand movement).

Figure 11:
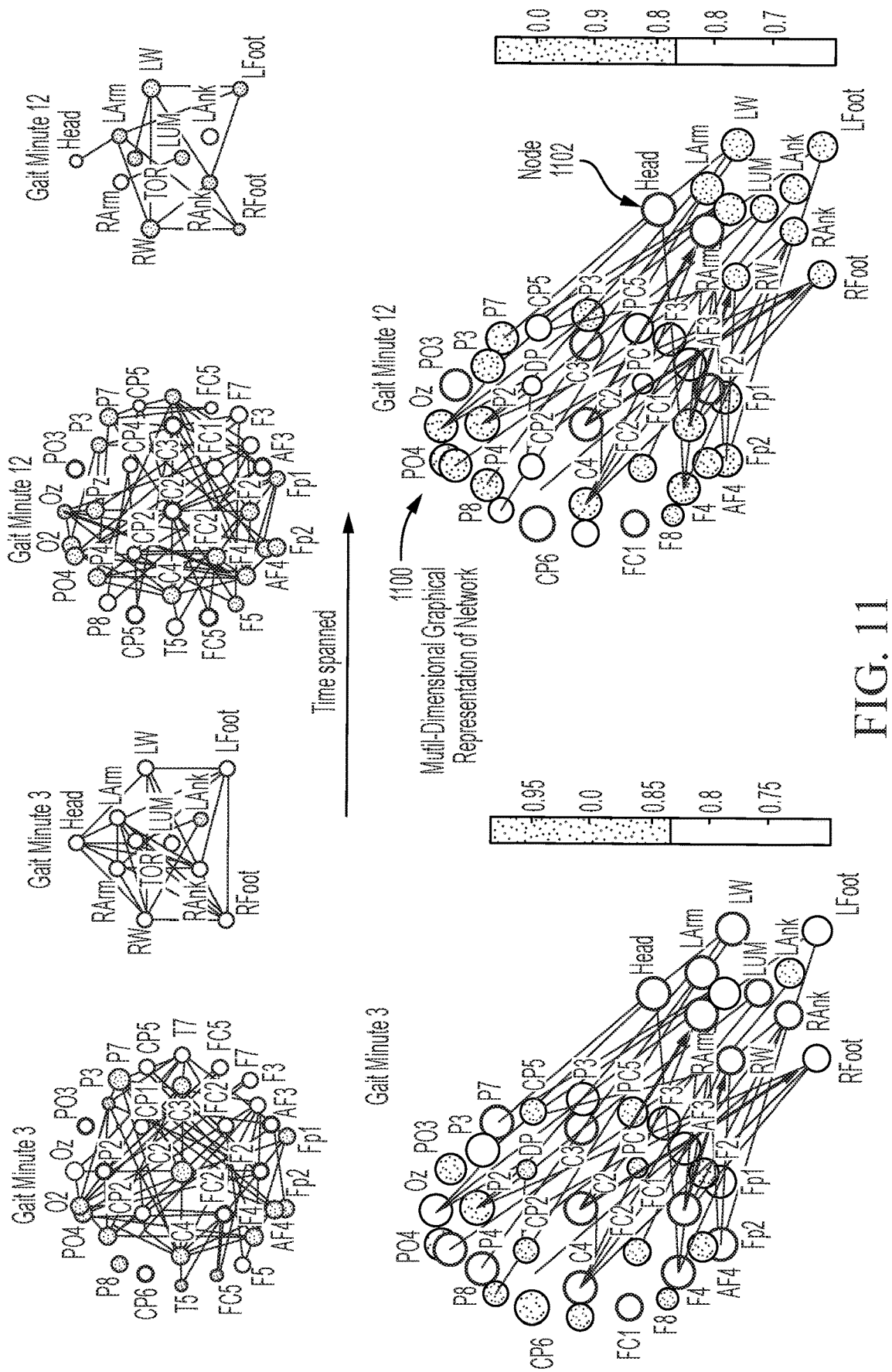
FIG. 11 illustrates an example of a multi-dimensional graphical representation of a full brain-body network showing the module between different brain-body activities as well synergistic activities within the brain networks and the body networks.

The system may filter the phase angle data to only include the data indicating a leading part 230 (i.e., brain leading body, body leading brain, or both in tandem). For example, the filtered data indicates that a first bodily activity (e.g., brain activity) is leading a second bodily activity (e.g., hand movements). The system may then use the filtered data to generate a multi-dimensional graphical representation of a network defined by the adjacency matrix 232. The network includes a plurality of nodes, e.g., nodes 1102 of FIG. 11. Each node represents a sensor coupled to the subject. The system may build the adjacency matrix from the peaks of the cross-spectrum coherence obtained pairwise between each brain and body nodes, including, for example, 31 nodes in the brain and 11 on the body. For each minute, the system may extract the maximum coherence value for each pair of nodes, along with the corresponding phase (via cross-spectral power density) and frequency values, and visually present these values in the form of matrices. Each entry of the coherence matrix contains the max coherence value during a minute time-frame for each pair of nodes represented in the rows and columns. In the instant example, the first 31 items of rows and columns belong to nodes within the brain network, and the next 11 items belong to nodes within the body network. The phase lead-lag matrix contains the phase (degrees) value when the maximum coherence value occurs between the corresponding pair of nodes. The frequency matrix contains the frequency value when the maximum coherence value occurs between the corresponding pair of nodes. The matrices thus obtained are the adjacency matrices used to build a weighted directed graph representing the full brain-body network, as shown in FIG. 12.

The multi-dimensional graphical representation shows the module between the different bodily activities. The arrows show which node is the leading node of each pair of nodes, and which node is the lagging node of each pair of nodes. An example of a multi-dimensional graphical representation of a network 1100 state is provided in FIG. 11. The multi-dimensional graphical representation enables one to identify sub-networks of nodes which work in tandem (depicted using circles of different colors whereby the edge of the circle reflects the coherence value along the color bar and the size of the circle gives the degree of the node, i.e., the number of links passing through the node in and out of it).

Figure 12:
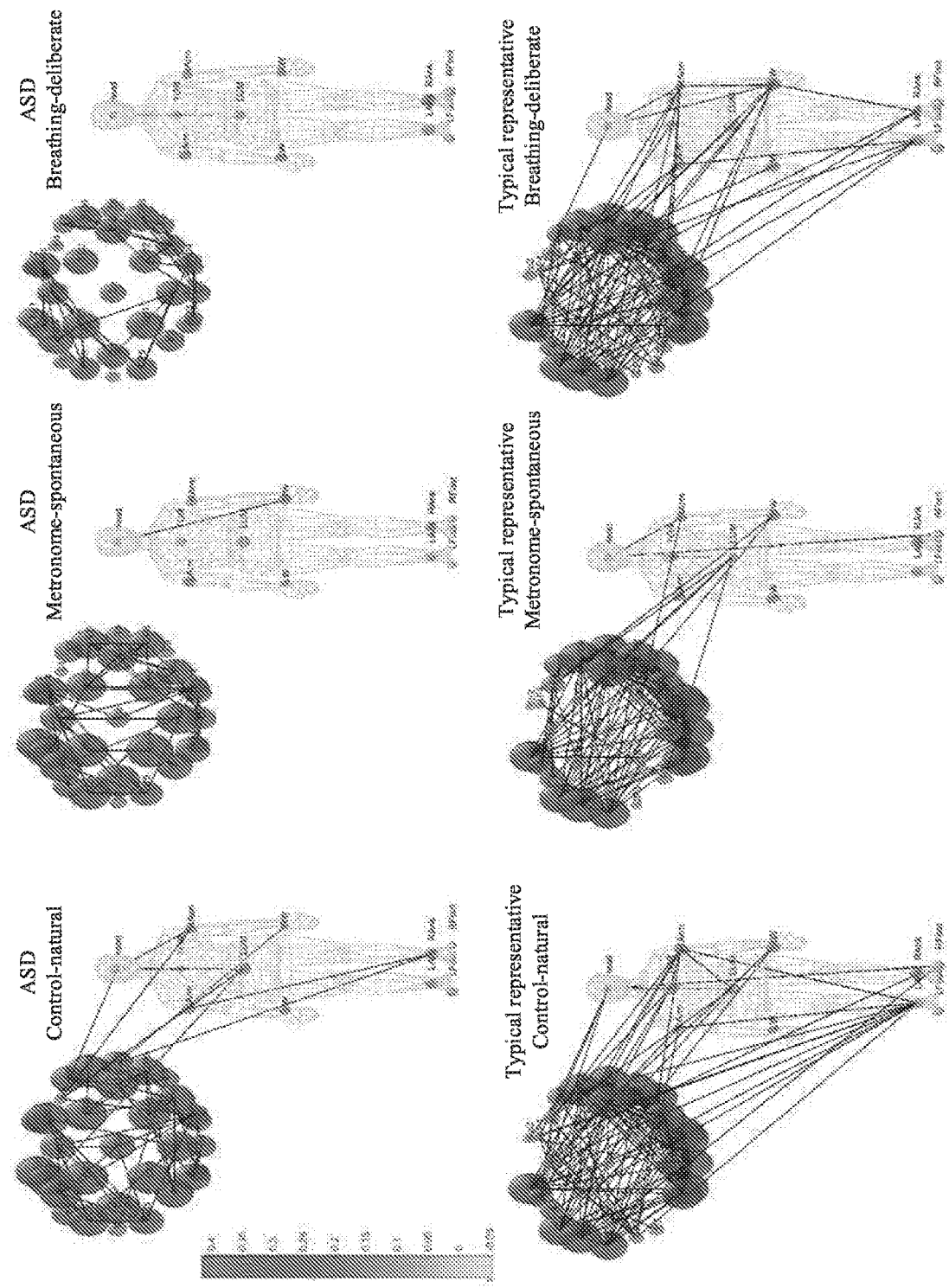
FIG. 12 illustrates an example of the coupled dynamics of the brain-body network unfolding in time for three different conditions.

FIG. 12 shows the coupled dynamics of the brain-body network unfolding in time for three different conditions: condition 1 is during a natural walk (left); condition 2 is in the presence of a metronome which spontaneously entrains the brain-body biorhythms in the typical case (middle); and condition 3 where the person is instructed to deliberately breathe to the rhythm of the metronome (right). The top row is an ASD participant where the brain-body coupled dynamics are sparse. The bottom row is a typical representative of far brain-body coupling and well-delineated brain regions devoted to the tasks. In contrast, the ASD participant lacks the entrainment with the external rhythms and with the breathing rhythms.

Figure 13:
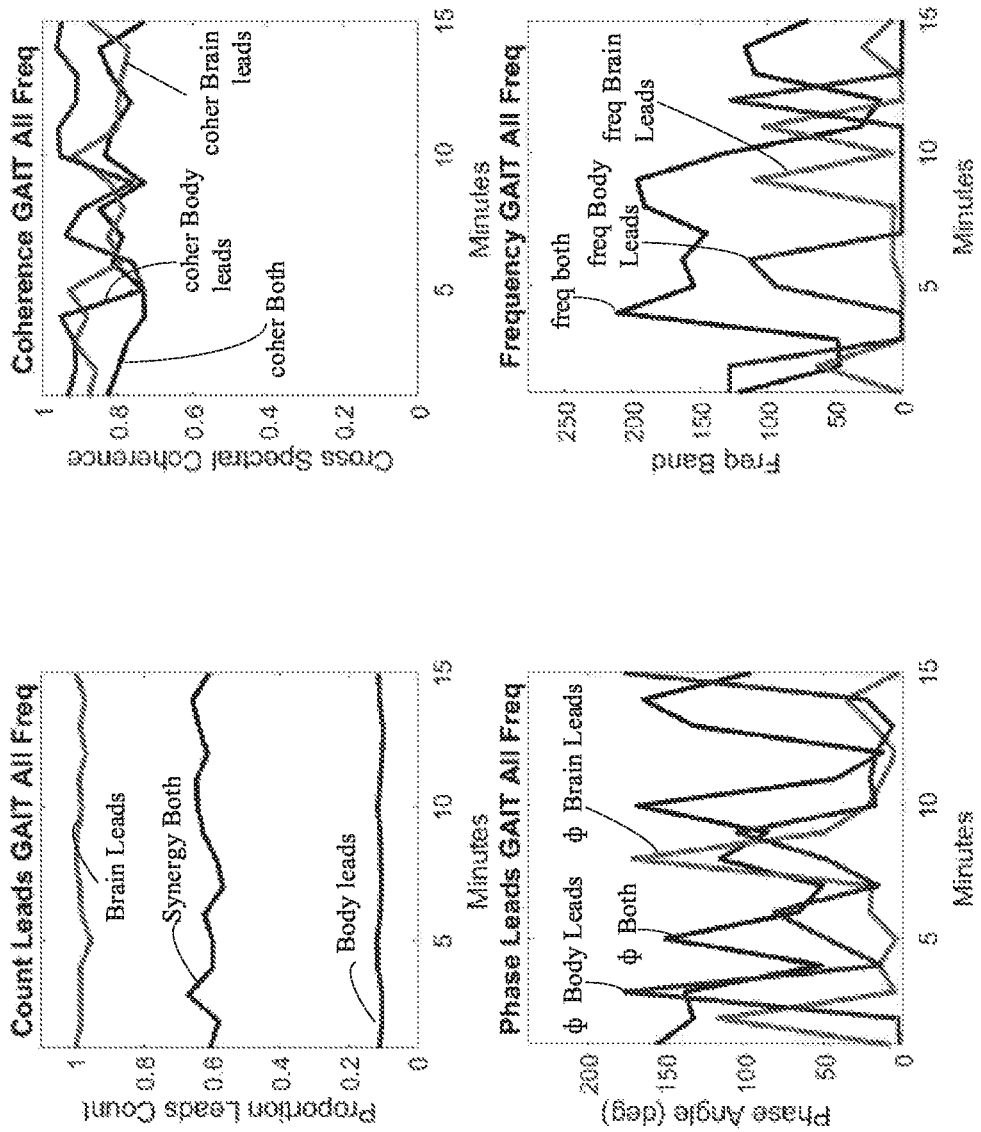
FIG. 13 illustrates an example of synchronous patterns of activities.

Referring to FIG. 2B, the system may use the synchronous patterns of activities associated with node pairs of the sub-networks to determine the amount of volition in the subject's body that is coming from the brain, the amount of feedback from the body, and/or the balance or bridge between the brain and body such that intent (brain) leads to deliberate volition (body) 234 (Graphs showing example of synchronous patterns of activities are provided in FIG. 13). The system may then use this amount of volition to determine a diagnosis and/or treatment plan for the subject 236. The system may also use other information in this step. This other information includes, but is not limited to, mental intent, physical volition, and the balance between mental intent and physical volition.

Figure 2C:
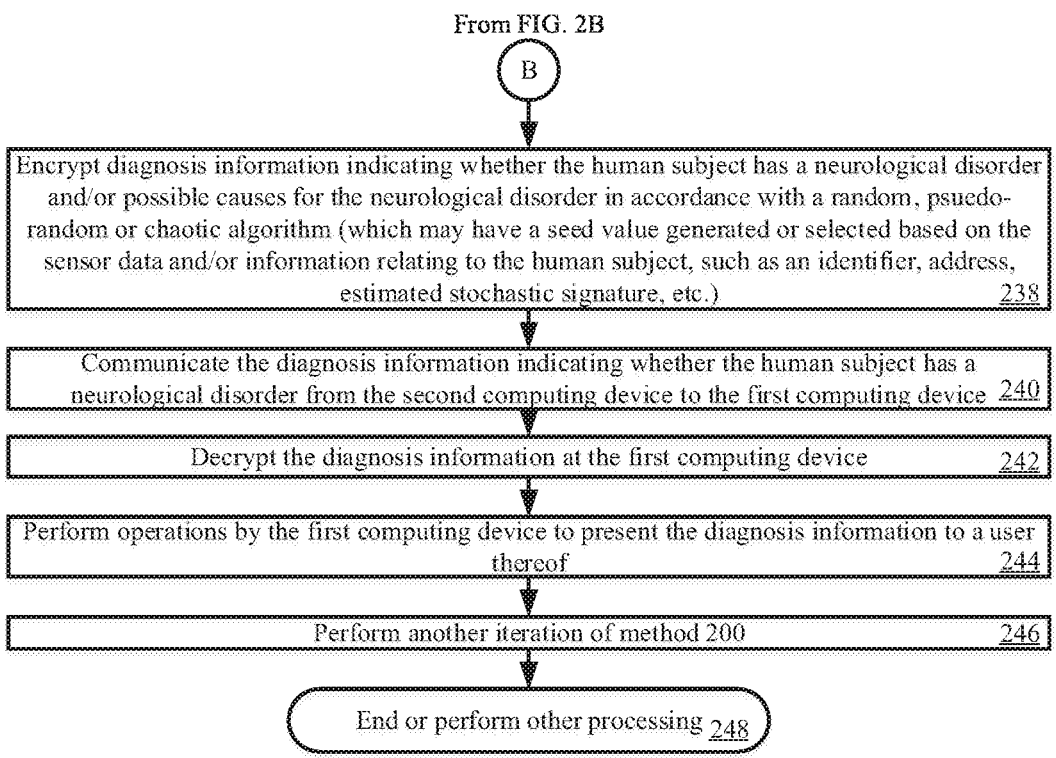

With reference to FIG. 2C, the system may optionally encrypt the diagnosis/treatment information 238. The encryption is achieved by a chaotic, random or pseudo-random based algorithm for generating a numerical sequence. Any known or to be known chaotic, random or pseudo-random number based algorithm can be used herein without limitation. A seed value for the chaotic, random or pseudo-random number based algorithm can be selected from a plurality of pre-defined seed values or dynamically generated during operations of the second computing device. The seed value(s) can be selected from or generated based on the sensor data and/or information relating to the human or animal subject (e.g., an identifier, an address, a phone number, an age, a medical diagnosis, a medical symptom, information contained in a medical history, the estimated stochastic signature, a mean value, a variance value, an NSR value, a level of randomness value, a value indicating a positive or negative change in the stochastic signature, moment values, etc.). The system may further communicate the diagnosis information from a second computing device to a first computing device via the network. At the first computing device, the system may decrypt the diagnosis information 242. Any suitable known or to be known decryption technique can be used herein without limitation.

The first computing device may perform operations to present the diagnosis information to a user thereof 244. The system may present the diagnosis information via a display, a speaker, or other output devices of the first computing device. The system may also present the diagnosis information to the user in an auditory format, visual format (e.g., a textual format, a graphical format, a table format and/or a chart format), and/or tactile format (e.g., as vibration). The system may use the diagnosis information to select a treatment plan that is appropriate and is likely to be most effective for the human or animal subject, and which has had a history of improving the same neurological disorder in other individuals with similar or the same test results (e.g., stochastic signatures).

In some scenarios, the method 200 may further include another iteration 246.

Figure 4:
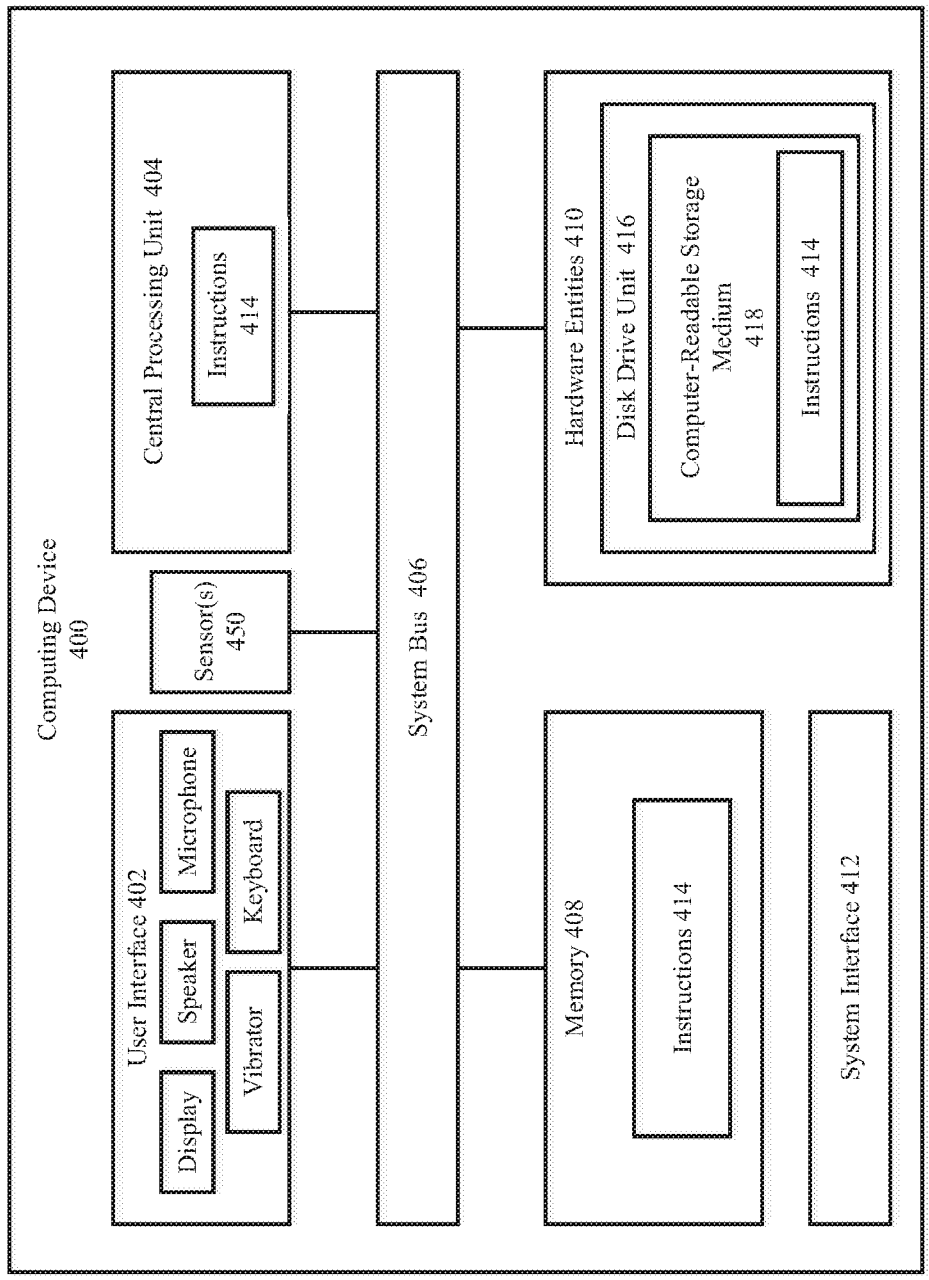
FIG. 4 illustrates an example of an architecture for a computing device.

The above-illustrated steps can be implemented in one or more computing systems. Referring now to FIG. 4, a computing system 400 is generally configured to perform operations for facilitating the connection of peripheral and central nerves output signatures of variability through the same statistical platform. As such, the computing system 400 includes a plurality of components 402-412. The computing system 400 can include more or fewer components than those shown in FIG. 4. However, the components shown are sufficient to disclose an illustrative embodiment implementing the present solution.

The hardware architecture of FIG. 4 represents one (1) embodiment of a representative computing device configured to facilitate the connection of peripheral and central nerves output signatures of variability through the same statistical platform. As such, the computing system 400 implements methods of the present solution.

The computing system 400 may include a system interface 412, a user interface 402 (e.g., a keyboard for data input and a display for data output), a Central Processing Unit ("CPU") 404, a system bus 406, a memory 408 connected to and accessible by other portions of the computing system 400 through system bus 406, and hardware entities 410 connected to system bus 406. At least some of the hardware entities 410 perform actions involving access to and use of memory 408, which can be a Random Access Memory ("RAM"), a disk driver and/or a Compact Disc Read Only Memory ("CD-ROM"). System interface 412 allows the computing system 400 to communicate directly or indirectly with external devices (e.g., sensors, servers, and client computers).

The computing device 400 may also include sensors 450. The present solution is not limited in this regard. For example, in other scenarios, the sensors are separate devices from the computing device 400. A communications link (wired or wireless) is provided for enabling communications between the computing device 400 and sensors. In all cases, sensors 450 are coupled to a human or animal subject for obtaining data from at least one physiological relevant signal of the subject. The sensor can include, but is not limited to, an accelerometer, a gyroscope, a motion sensor, a vibration sensor, a position sensor, a restoration sensor, and/or a medical sensor (e.g., an electromyography sensor, an electrocardiogram sensor, an RIP sensor, an MRI sensor, etc.).

Hardware entities 410 may include microprocessors, Application Specific Integrated Circuits ("ASICs") and other hardware. Hardware entities 410 can include a microprocessor programmed to facilitate the connection of peripheral and central nerves output signatures of variability through the same statistical platform.

The hardware entities 410 may include a disk drive unit 416 including a computer-readable storage medium 418 on which is stored one or more sets of instructions 414 (e.g., software code) configured to implement one or more of the methodologies, procedures, or functions described herein. The instructions 414 can also reside, completely or at least partially, within the memory 408 and/or the CPU 404 during execution thereof by the computing system 400. The components 408 and 404 also can constitute machine-readable media. The term "machine-readable media." as used here, refers to a single medium or multiple media (e.g., a centralized or distributed database, and/or associated caches and servers) that store the one or more sets of instructions 414. The term "machine-readable media." as used here, also refers to any medium that is capable of storing, encoding or carrying a set of instructions 414 for execution by the computing system 400 and that cause the computing system 400 to perform any one or more of the methodologies of the present disclosure.

Notably, the present solution can be implemented in a single computing device as shown in FIG. 4. The present solution is not limited in this regard. Alternatively, the present solution can be implemented in a distributed network system. For example, the present solution can take advantage of multiple CPU cores over a distributed network of computing devices in a cloud or cloud-like environment. The distributed network architecture ensures that the computing time of the statistics and enhanced functionality is reduced to a minimum, allowing end-users to perform more queries and to receive reports at a faster rate. The distributed network architecture also ensures that the implementing software is ready for being deployed on an organization's internal servers or cloud services in order to take advantage of its scaling abilities (e.g., request more or fewer CPU cores dynamically as a function of the quantity of data to process or the number of parameters to evaluate).

In view of the foregoing, the present solution provides an analytical tool for stochastic measurement of dynamic signals from cephalic probes as well as peripheral probes. The tool provides a statistically estimated individual signature that: (a) can be evaluated against a benchmark in order to have assessments about an abnormal condition, a condition deterioration, and a prognosis; (b) provides an aid for diagnostic purposes; (3) provides a capability to engage a neuro-motor function efficiently; and (4) provide a differentiating way in development of specialized skills. The present solution has applicability in the following areas: neuroimaging and disorders of consciousness; aid to diagnosis of neuro-motor disorders; prognostic and evaluation of recovery; research, imaging, and disorders of consciousness; brain-typing/personal identity traits; and/or legal and forensic issues.

All of the apparatus, methods, and algorithms disclosed and claimed herein can be made and executed without undue experimentation in light of the present disclosure. While the invention has been described in terms of preferred embodiments, it will be apparent to those having ordinary skill in the art that variations may be applied to the apparatus, methods, and sequence of steps of the method without departing from the concept, spirit, and scope of the invention. More specifically, it will be apparent that certain components may be added to, combined with, or substituted for the components described herein while the same or similar results would be achieved. All such similar substitutes and modifications apparent to those having ordinary skill in the art are deemed to be within the spirit, scope, and concept of the invention as defined.

The features and functions disclosed above, as well as alternatives, may be combined into many other different systems or applications. Various presently unforeseen or unanticipated alternatives, modifications, variations or improvements may be made by those skilled in the art, each of which is also intended to be encompassed by the disclosed embodiments.

What is claimed is:

1. A system for providing a medical diagnosis, comprising:
   a first sensor attachable to a head of a subject and configured to measure a first rhythm of the subject over a first recording time and generate a first sub-second time series of sensor data of the subject comprising one or more micro-rhythm waveforms with a sub-second temporal resolution;
   a second sensor attachable to a body part of the subject and configured to measure a second rhythm of the subject over a second recording time and generate a second sub-second time series of sensor data of the subject comprising one or more micro-rhythm waveforms with a sub-second temporal resolution;
   a processor; and
   a non-transitory computer readable medium containing programming instructions that, when executed, cause the processor to:
      perform a power spectral analysis of a first micro-rhythm waveform in the first sub-second time series of sensor data and a second micro-rhythm waveform in the second sub-second time series of sensor data to identify a coherence therebetween, and
      determine an amount of volition in the subject's body based on the coherence.

2. The system of claim 1, wherein the first sensor comprises one or more electrodes of an ElectroEncephaloGram ("EEG") device.

3. The system of claim 2, wherein the programming instructions comprise additional programming instructions configured to cause the processor to, before performing the power spectral analysis:
   determine a Noise-to-Signal Ratio ("NSR") over the first and second recording time for each of the one or more micro-rhythm waveforms; and
   re-reference each of the micro-rhythm waveforms by subtracting therefrom an NSR corresponding to a sensor having a lowest average NSR over the recording time among all of the one or more micro-rhythm waveforms in the first and second sub-second time series of sensor data.

4. The system of claim 3, wherein the programming instructions for determining the NSR for each of the one or more micro-rhythm waveforms comprise programming instructions configured to cause the processor to:
   estimate moments of a continuous family of a probability distribution function for each of the one or more micro-rhythm waveforms in the first and second sub-second time series of sensor data; and
   use the estimated moments to determine the NSR.

5. The system of claim 4, wherein the probability distribution function is a Gamma function, a Gaussian distribution function, or a lognormal distribution function.

6. The system of claim 4, wherein the probability distribution function is a Gamma function, and the estimated moments comprise an estimated scale parameter of the Gamma function.

7. The system of claim 1, wherein the second sensor is an accelerometer, a gyroscope, a motion sensor, a vibration sensor, a position sensor, a restoration sensor, an electromyography sensor, an electrocardiogram sensor, a RIP sensor, or an MRI sensor.

8. The system of claim 1, wherein the second sensor is attached to a hand, a foot, a leg, a chest, a waist, an arm, or ankle of the subject.

9. The system of claim 1, wherein the programming instructions comprise additional programming instructions configured to cause the processor to:
   normalize each of the one or more micro-rhythm waveforms in the first and second sub-second time series of sensor data to generate a corresponding normalized micro-rhythm waveform, before performing the power spectral analysis, wherein each normalized micro-rhythm waveform is unitless and scaled from zero to one.

10. The system of claim 1, wherein the programming instructions for determining the amount of volition comprise programming instructions configured to cause the processor to:
    generate a first spectrogram from the first micro-rhythm waveform and a second spectrogram from the second micro-rhythm waveform;
    compare the first spectrogram and the second spectrogram to:
       generate a cross-spectrum coherence graph representing the coherence between the first and second micro-rhythm waveforms, wherein the cross-spectrum coherence graph comprises a plurality of peaks along a frequency axis, each peak indicating a frequency at which the first micro-rhythm waveform and the second micro-rhythm waveform are coherent,
       generate a phase angle graph representing phase angle values along the frequency axis;
    for each two successive peaks in the cross-spectrum coherence graph:
       determine a polarity of a phase angle value between two frequencies where each of the two successive peaks is located, and
       determine whether a bodily activity associated with the first sensor is leading or lagging a bodily activity associated with the second sensor based on the polarity of the phase angle value.

11. The system of claim 10, further comprising additional programming instructions configured to cause the processor to generate a network including a plurality of nodes and a plurality of links, wherein:
    each node represents a sensor coupled to the subject,
    each link connects between a first and second node, the link representing a module between bodily activities measured by a sensor associated with the first node and bodily activities measured by a sensor associated with the second node.

12. The system of claim 11, further comprising additional programming instructions configured to cause the processor to generate a multi-dimensional graphical representation of the network, wherein:
    each node is represented by a circle, wherein a color of the circle represents a coherence value along a color bar; and
    each circle has a size that represents a number of links passing through the node represented by the circle.

13. The system of claim 1, further comprising a display, wherein the programming instructions comprise additional programming instructions configured to cause the processor to:

determine a diagnosis or a treatment plan for the subject based on the amount of volition; and output the diagnosis or the treatment plan on the display.

14. The system of claim 1, wherein the first and second sensor are further attachable to a head and a body part of one or more additional subjects in a social group, respectively, and the programming instructions for determining the amount of volition in the subject's body are also configured to determine the amount of volition in the one or more additional subjects in the social group.

15. The system of claim 14, wherein the social group comprises a social interaction group, a sports group or a ballet performance group.

16. A method for providing a medical diagnosis, comprising:

measuring, by a first sensor attachable to a head of a subject, a first rhythm of the subject over a first recording time and generating a first sub-second time series of sensor data of the subject comprising one or more micro-rhythm waveforms with a sub-second temporal resolution;

measuring, by a second sensor attachable to a body part of the subject, a second rhythm of the subject over a second recording time and generating a second sub-second time series of sensor data of the subject comprising one or more micro-rhythm waveforms with a sub-second temporal resolution;

performing, by a processor, a power spectral analysis of a first micro-rhythm waveform in the first sub-second time series of sensor data and a second micro-rhythm waveform in the second sub-second time series of sensor data to identify a coherence therebetween; and determining an amount of volition in the subject's body based on the coherence.

17. The method of claim 16, further comprising:

normalizing, by the processor, each of the one or more micro-rhythm waveforms in the first and second sub-second time series of sensor data to generate a corresponding normalized micro-rhythm waveform, before performing the power spectral analysis, wherein each normalized micro-rhythm waveform is unitless and scaled from zero to one.

18. The method of claim 16, further comprising:

generating, by the processor, a first spectrogram from the first micro-rhythm waveform and a second spectrogram from the second micro-rhythm waveform;

comparing, by the processor, the first spectrogram and the second spectrogram to:

generate a cross-spectrum coherence graph representing the coherence between the first and second micro-rhythm waveforms, wherein the cross-spectrum coherence graph comprises a plurality of peaks along a frequency axis, each peak indicating a frequency at which the first micro-rhythm waveform and the second micro-rhythm waveform are coherent, generate a phase angle graph representing phase angle values along the frequency axis;

for each two successive peaks in the cross-spectrum coherence graph:

identify a synchronous pattern between the two successive peaks, determine a polarity of a phase angle value between two frequencies where each of the two successive peaks are located, and determine whether a bodily activity associated with the first sensor is leading or lagging a bodily activity associated with the second sensor based on the polarity of the phase angle value.

19. The method of claim 16, further comprising:

determining, by the processor, a diagnosis or a treatment plan for the subject based on the amount of volition; and outputting, by the processor, the diagnosis or the treatment plan on the display.

20. The method of claim 16, further comprising:

measuring, by the first and second sensor attached to a head and a body part of one or more additional subjects in a social group, respectively, sensor data for the one or more additional subjects, each sensor data comprising one or more micro-rhythm waveforms;

performing, by the processor, for each of the one or more additional subjects, a power spectral analysis of a micro-rhythm waveform in the sensor data measured by the first sensor and a micro-rhythm waveform in the sensor data measured by the second sensor to identify a coherence therebetween; and using the coherence to determine an amount of volition in each of the one or more additional subjects in the social group.

* * * * *